(12) United States Patent
Keenan et al.

(10) Patent No.: US 9,320,470 B2
(45) Date of Patent: Apr. 26, 2016

(54) METHOD AND/OR SYSTEM FOR SENSOR ARTIFACT FILTERING

(75) Inventors: Desmond Barry Keenan, Los Angeles, CA (US); John J. Mastrototaro, Los Angeles, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 1295 days.

(21) Appl. No.: 12/347,716

(22) Filed: Dec. 31, 2008

(65) Prior Publication Data

US 2010/0168538 A1    Jul. 1, 2010

(51) Int. Cl.
| | |
|---|---|
| *A61B 5/145* | (2006.01) |
| *G01N 33/49* | (2006.01) |
| *G06F 15/00* | (2006.01) |
| *A61B 5/00* | (2006.01) |
| *A61B 5/07* | (2006.01) |
| *A61B 5/15* | (2006.01) |
| *A61B 5/1486* | (2006.01) |
| *A61M 5/142* | (2006.01) |
| *A61M 5/172* | (2006.01) |

(52) U.S. Cl.
CPC ............ *A61B 5/6848* (2013.01); *A61B 5/0031* (2013.01); *A61B 5/07* (2013.01); *A61B 5/1411* (2013.01); *A61B 5/14532* (2013.01); *A61B 5/14865* (2013.01); *A61B 5/4839* (2013.01); *A61B 5/6849* (2013.01); *A61M 5/14244* (2013.01); *A61M 5/1723* (2013.01); *A61M 2205/3569* (2013.01); *A61M 2205/3592* (2013.01); *A61M 2230/201* (2013.01)

(58) Field of Classification Search
CPC ........................ A61B 5/14532; C12Q 1/006
See application file for complete search history.

(56) References Cited

U.S. PATENT DOCUMENTS

| | | | |
|---|---|---|---|
| 4,171,909 A | * | 10/1979 | Kramer et al. ............... 356/73 |
| 6,067,463 A | * | 5/2000 | Jeng et al. .................. 600/336 |
| 6,254,586 B1 | | 7/2001 | Mann |
| 6,424,847 B1 | | 7/2002 | Mastrototaro |
| 6,641,533 B2 | | 11/2003 | Causey, III |
| 6,895,263 B2 | | 5/2005 | Shin |
| 7,267,665 B2 | | 9/2007 | Steil et al. |
| 7,833,157 B2 | | 11/2010 | Gottlieb |
| 2005/0043598 A1 | | 2/2005 | Goode |
| 2005/0059871 A1 | | 3/2005 | Gough |
| 2008/0103535 A1 | | 5/2008 | Ostroff |
| 2008/0221509 A1 | | 9/2008 | Gottlieb et al. |

FOREIGN PATENT DOCUMENTS

WO    WO00/74753    12/2000

OTHER PUBLICATIONS

Van Den Berghe, Greet, et al., "Intensive Insulin Therapy in Critically Ill Patients" The New England Journal of Medicine, vol. 345, No. 19, Nov. 8, 2001, pp. 1359-1367.
PCT/US2009/006679/ Copy of PCT application as filed on Dec. 22, 2009, 56 pages.
PCT/US2009/006679/ Initial Publication with International Search Report on Jul. 8, 2010, 59 pages.
PCT/US2009/006679/ International Search Report mailed Apr. 6, 2010, 4 pages.
PCT/US2009/006679/ Written Opinion of the International Search Authority, mailed Jun. 30, 2011, 4 pages.
PCT/US2009/006679/ International Preliminary Report on Patentability mailed Jul. 5, 2011, 5 pages.
EP09803943.1 / Copy of amended claims filed with nationalized EP application, filed Jun. 3, 2011, 4 pages.
EP09803943.1 / EPO communication regarding written opinion/ amendment mailed Aug. 9, 2011, 2 pages.

* cited by examiner

*Primary Examiner* — Kenneth R. Horlick
*Assistant Examiner* — David Thomas
(74) *Attorney, Agent, or Firm* — Berkeley Law & Technology Group, LLP

(57) ABSTRACT

Disclosed are a method and/or system for filtering sensor measurements. In one particular implementation, a sensor signal may be processed concurrently in a plurality of signal-filter paths. A particular signal-filter path may be selected to provide an output signal for obtaining a measurement based, at least in part, on a measurement of noise associated with the sensor signal.

26 Claims, 21 Drawing Sheets

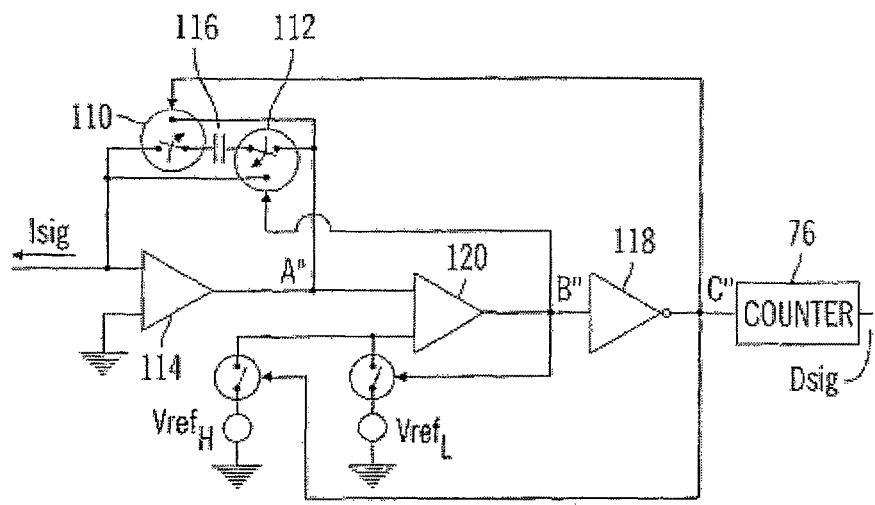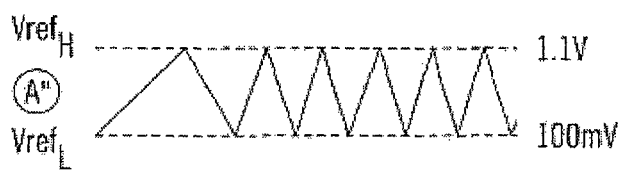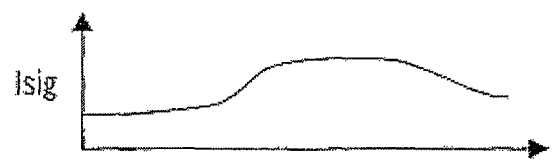
FIG. 13
FIG. 12

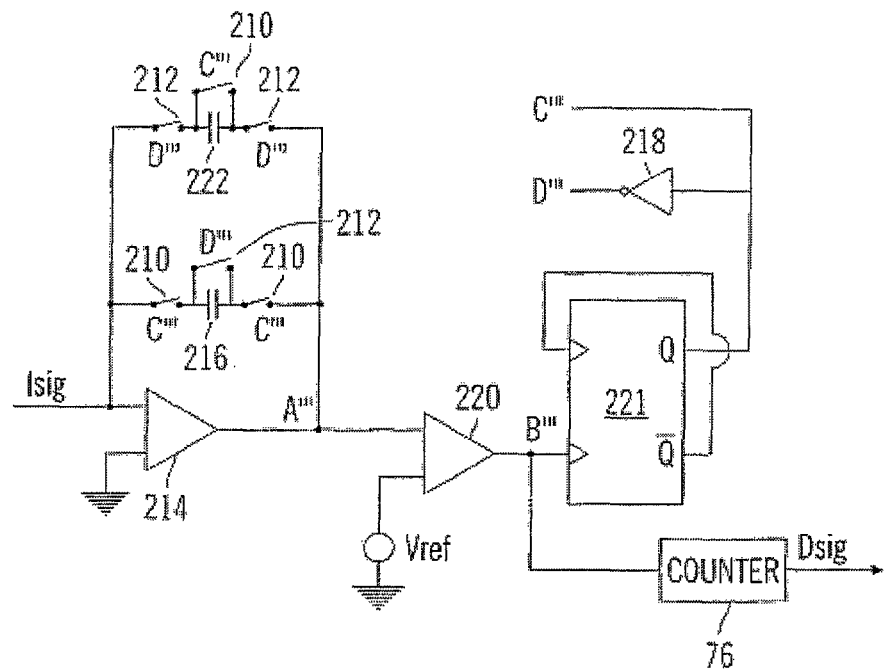
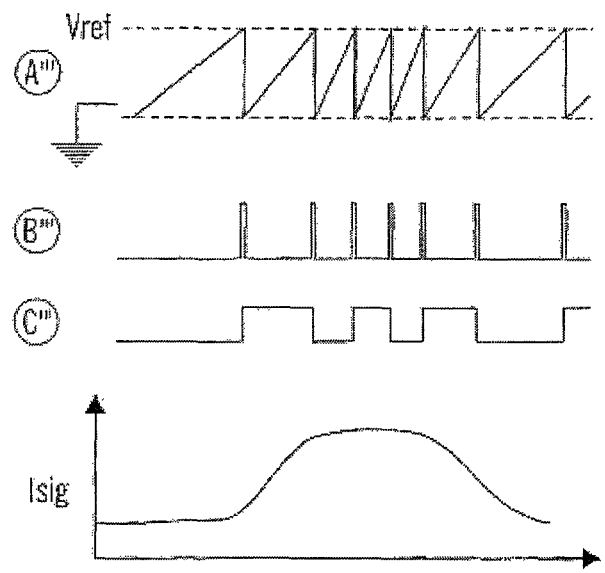
FIG. 14
FIG. 13

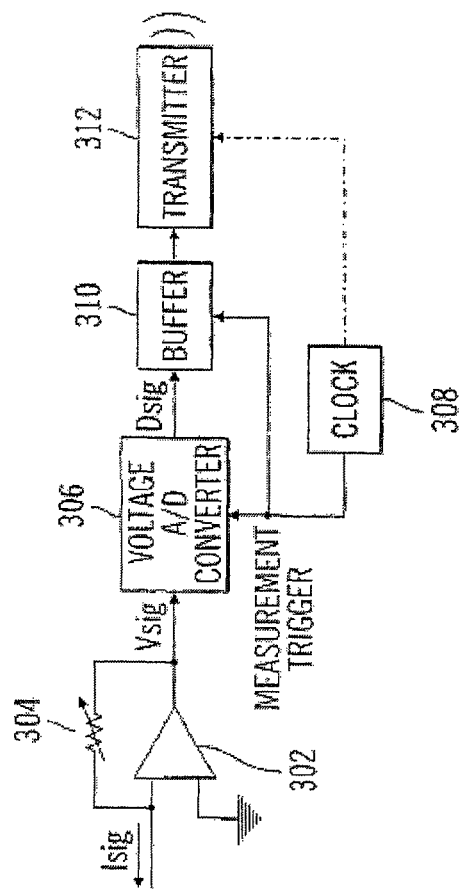
FIG. 14
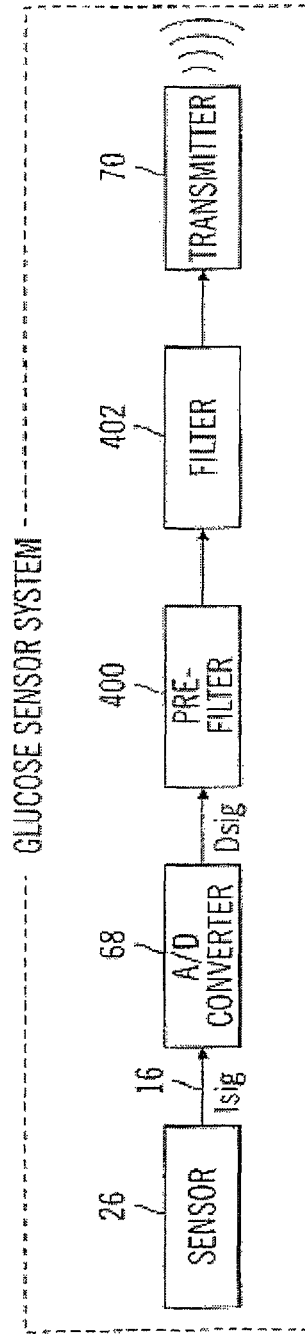
FIG. 15
FIG. 16

METHOD AND/OR SYSTEM FOR SENSOR ARTIFACT FILTERING

BACKGROUND

1. Field

Subject matter disclosed herein relates to processing signals from sensors used to measure blood-glucose levels in patients.

2. Information

The pancreas of a normal healthy person produces and releases insulin into the blood stream in response to elevated blood plasma glucose levels. Beta cells (β-cells), which reside in the pancreas, produce and secrete the insulin into the blood stream, as it is needed. If β-cells become incapacitated or die, a condition known as Type I diabetes mellitus (or in some cases if β-cells produce insufficient quantities of insulin, Type II diabetes), then insulin must be provided to the body from another source.

Traditionally, since insulin cannot be taken orally, insulin has been injected with a syringe. More recently, use of infusion pump therapy has been increasing, especially for delivering insulin to diabetics. For example, external infusion pumps are worn on a belt, in a pocket, or the like, and deliver insulin into the body via an infusion tube with a percutaneous needle or a cannula placed in the subcutaneous tissue. As of 1995, less than 5% of Type I diabetics in the United States were using infusion pump therapy. Presently over 7% of the more than 900,000 Type I diabetics in the U.S. are using infusion pump therapy. And the percentage of Type I diabetics that use an infusion pump is growing at an absolute rate of over 2% each year. Moreover, the number of Type I diabetics is growing at 3% or more per year. In addition, growing numbers of insulin using Type II diabetics are also using infusion pumps. Physicians have recognized that continuous infusion provides greater control of a diabetic's condition, and are also increasingly prescribing it for patients.

To deliver proper amounts of insulin to a patient, infusion pump systems typically obtain blood-glucose measurements form the patient in real-time using a blood-glucose sensor implanted in the patient. Such an implanted blood-glucose sensor typically generates a signal having a value that is representative of a blood-glucose concentration in a patient. Here, such a signal is typically processed and/or filtered to remove noise, etc. The processed signal may then be sampled to obtain an estimate of a blood-glucose concentration.

SUMMARY

Briefly, one embodiment relates to a method, system and/or apparatus for providing a signal representative of a blood glucose concentration; and selecting an output signal for use in estimating said blood glucose concentration from among a plurality of signal-filter paths based, at least in part, on a measurement of noise associated with said signal.

In a particular implementation, the method, system and/or apparatus may further perform generating said signal based upon a measurement of said blood glucose concentration; and obtaining said measurement of said noise contemporaneous with obtaining said measurement of said blood glucose concentration.

In another particular implementation, the plurality of signal-filter paths may comprise at least one signal-filter path with no filtering and at least one signal-filter path comprising a finite impulse response (FIR) filter. In a particular alternative, the method, system and/or apparatus may perform selecting said output signal from said at least one signal-filter path with no filtering if said measurement of said noise is below a threshold level.

In another particular implementation, the method, system and/or apparatus may further perform high-pass filtering said signal to provide an isolated noise component; and determining said measurement of noise based, at least in part, on said isolated noise component.

In another particular implementation, the method, system and/or apparatus may further perform receiving said signal representative of said blood-glucose concentration from a blood-glucose sensor implanted in a patient.

In another particular implementation, the method, system and/or apparatus may further perform selecting an output signal for use in estimating said blood glucose concentration from a different one of said plurality signal-filter paths based, at least in part, in a change in said measurement of noise.

In another particular implementation, at least one signal-filter path comprises a seventh-order FIR filter.

In an alternative implementation, at least one signal-filter path comprises an infinite impulse response filter.

In another alternative implementation, at least one signal-filter path comprises a Kalman filter.

Particular embodiments may be directed to an article comprising a storage medium including machine-readable instructions stored thereon which, if executed by a computing platform, are directed to enable the computing platform to execute at least a portion of the aforementioned method according to one or more of the particular aforementioned implementations. In other particular embodiments, a sensor adapted generate one or more signals responsive to a blood glucose concentration in a body while a computing platform is adapted to perform the aforementioned method according to one or more of the particular aforementioned implementations based upon the one or more signals generated by the sensor.

BRIEF DESCRIPTION OF THE FIGURES

Non-limiting and non-exhaustive features will be described with reference to the following figures, wherein like reference numerals refer to like parts throughout the various figures.

FIG. 12 is another circuit diagram of an I-F A/D converter of FIG. 9 accompanied by charts of node signals in accordance with an embodiment.

FIG. 13 is still another circuit diagram of an I-F A/D converter of FIG. 9 accompanied by charts of node signals in accordance with an embodiment.

FIG. 14 is a circuit diagram of an I-V A/D converter of FIG. 9 in accordance with an embodiment.

FIG. 15 is a block diagram of the glucose sensor system of FIG. 10 with a pre-filter and a filter in accordance with an embodiment.

DETAILED DESCRIPTION

Figure 1:
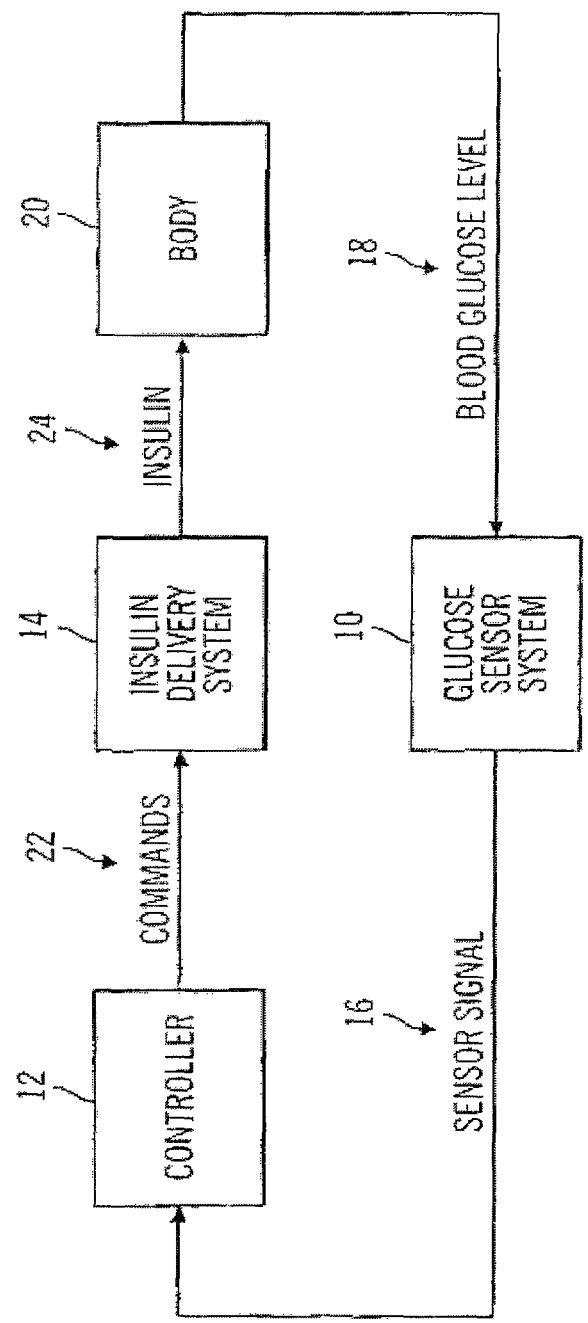
FIG. 1 is a block diagram of a closed loop glucose control system in accordance with one embodiment.

In one implementation, blood-glucose measurements are employed in a closed loop infusion system for regulating a rate of fluid infusion into a body. In particular embodiments, a control system is adapted to regulate a rate of insulin infusion into the body of a patient based, at least in part, on a glucose concentration measurement taken from the body (e.g., from a blood-glucose sensor). In particular implementations, such a system is designed to model a pancreatic beta cell (β-cell). Here, such a system may control an infusion device to release insulin into a body of a patient in a similar concentration profile as would be created by fully functioning human β-cells if responding to changes in blood glucose concentrations in the body.

Thus, such a closed loop infusion system may simulate a body's natural insulin response to blood glucose levels and, not only make efficient use of insulin, but also account for other bodily functions as well since insulin has both metabolic and mitogenic effects. However, the effectiveness of such a closed loop infusion system relies on the accuracy of an estimate of a blood-glucose concentration obtained from blood-glucose measurements taken from the patient. Such blood-glucose measurements may be taken using a blood-glucose sensor implanted in the patient. In one implementation, such a blood-glucose sensor may generate a sensor signal having a value that is associated with a blood-glucose concentration.

Various types of unwanted effects can interfere with continuous glucose sensor signal measurements such as electrical noise, physiological effects, movement artifact during ambulation, pressure changes and undesirable transient effects. If signals are processed in real-time by conventional digital filters it is desirable to reduce an amount of delay while reducing interference or noise. Real-time signals applied to digital filters, such as linear Finite Impulse Response (FIR) filters and nonlinear Infinite Impulse Response (IIR) filters, undergo a group delay stemming from particular filter design. For example, low-pass filters may have an increasing group delay with higher filter orders providing greater levels of attenuation, sharper transition widths and smaller pass band ripples. Therefore, such a delay may be roughly proportional to the level of robustness required of the filter. Less delay may be achieved by decreasing an amount of filtering, which maybe acceptable for raw signals having a reasonably high signal-to-noise ratio (SNR). If a greater level of noise is present, a longer delay may be unavoidable in order to filter a sufficient amount of noise from the signal.

In one example embodiment, a sensor provides a signal representative of a blood-glucose concentration in a patient. The signal may then be processed in a plurality of signal-filter paths to provide a plurality of associated candidate output signals. Based at least in part on a measurement of noise associated with the signal, one of the candidate output signals is selected for use in obtaining a measurement of a blood-glucose concentration. It should be understood, however, that this is merely an example embodiment and that claimed subject matter is not limited in this respect.

By selecting an output signal from among a plurality of signal-filter paths, group delays incurred during signal segments with high SNRs may be decreased by employing lower levels of filtering in the signal-filter path associated with the selected output signal. In one particular implementation, such a signal-filter path is chosen by first detecting noise and measuring the noise amplitude. If very low levels of noise are present, minimal filtering or no filtering is applied and therefore minimal delay is introduced. With increased levels of noise, however, filters with a higher degree of noise rejection in a different signal-filter path may be used, thereby introducing a longer group delay.

Particular embodiments include a glucose sensor system 10, a controller 12 and an insulin delivery system 14, as shown in FIG. 1. Glucose sensor system 10 generates a sensor signal 16 representative of blood glucose levels 18 in body 20, and provides sensor signal 16 to controller 12. Controller 12 receives sensor signal 16 and generates commands 22 that are communicated to insulin delivery system 14. Insulin delivery system 14 receives commands 22 and infuses insulin 24 into body 20 in response to commands 22.

Glucose sensor system 10 includes a glucose sensor, sensor electrical components to provide power to sensor and generate the sensor signal 16, a sensor communication system to carry sensor signal 16 to controller 12, and a sensor system housing for the electrical components and the sensor communication system.

Controller 12 may include electrical components and software to generate commands for the insulin delivery system 14 based on sensor signal 16, and a controller communication system to receive sensor signal 16 and carry commands to insulin delivery system 14.

Insulin delivery system 14 may include an infusion device and an infusion tube to infuse insulin 24 into body 20. In particular embodiments, the infusion device includes infusion electrical components to activate an infusion motor according to commands 22, an infusion communication system to receive commands 22 from controller 12, and an infusion device housing to hold the infusion device.

In particular embodiments, controller 12 may be housed in an infusion device housing, and an infusion communication system may comprise an electrical trace or a wire that carries commands 22 from controller 12 to the infusion device. In alternative embodiments, controller 12 may be housed in a sensor system housing and the sensor communication system may comprise an electrical trace or a wire that carries the sensor signal 16 from sensor electrical components to controller electrical components. In other alternative embodiments, controller 12 has its own housing or is included in a supplemental device. In another alternative embodiment, controller 12 is located with an infusion device and a sensor system all within one housing. In further alternative embodiments, the sensor, controller, and/or infusion communication systems may utilize a cable, a wire, fiber optic lines, RF, IR, or ultrasonic transmitters and receivers, and/or the like instead of electrical traces.

System Overview

Figure 2:
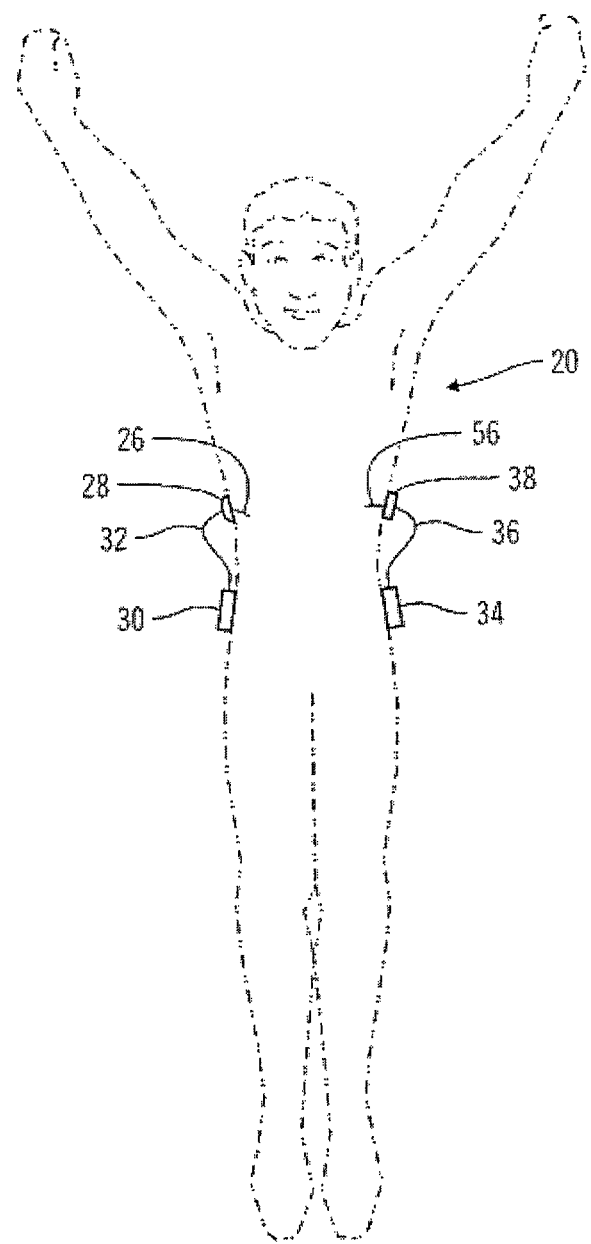
FIG. 2 is a front view of closed loop hardware located on a body in accordance with an embodiment.
Figure 3:
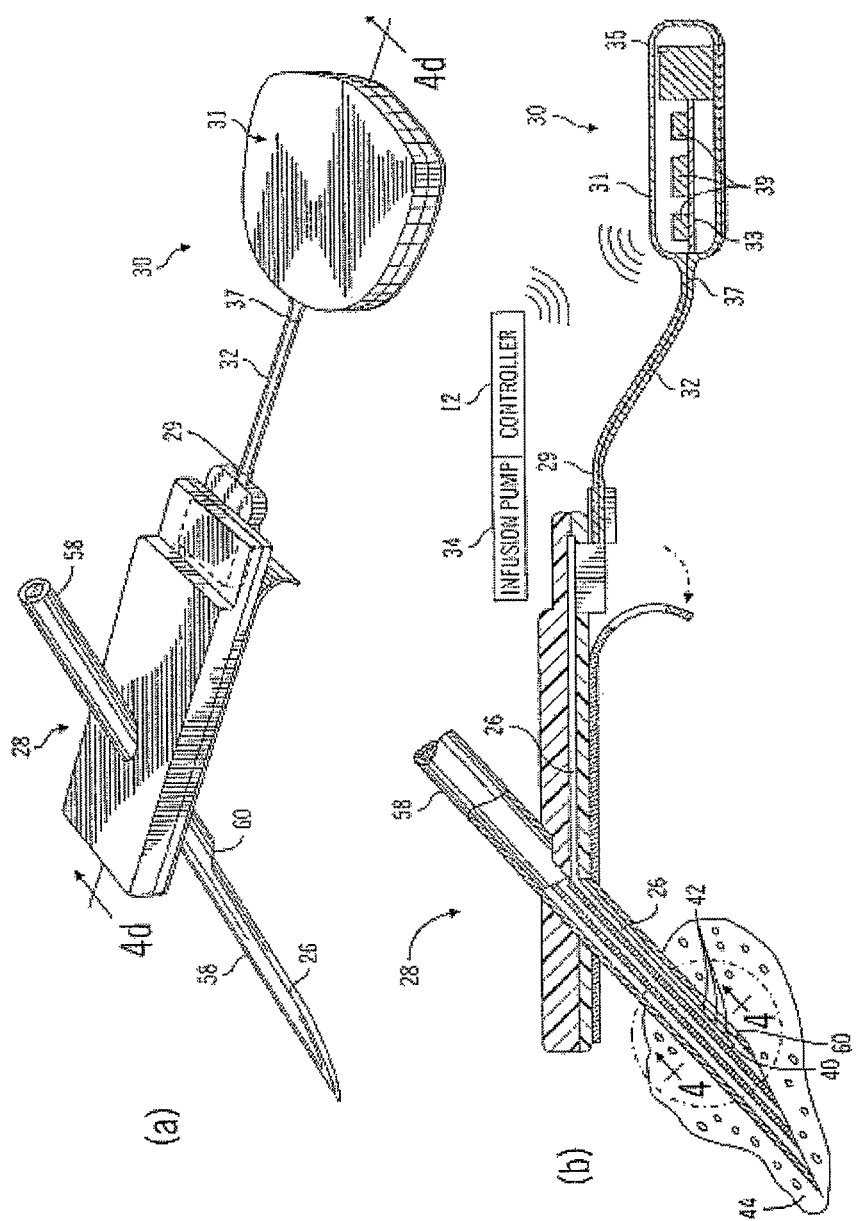
FIG. 3(a) is a perspective view of a glucose sensor system for use in an embodiment.
FIG. 3(b) is a side cross-sectional view of the glucose sensor system of FIG. 3(a).
FIG. 3(c) is a perspective view of a sensor set of the glucose sensor system of FIG. 3(a) for use in an embodiment.
FIG. 3(d) is a side cross-sectional view of the sensor set of FIG. 3(c).
Figure 3:
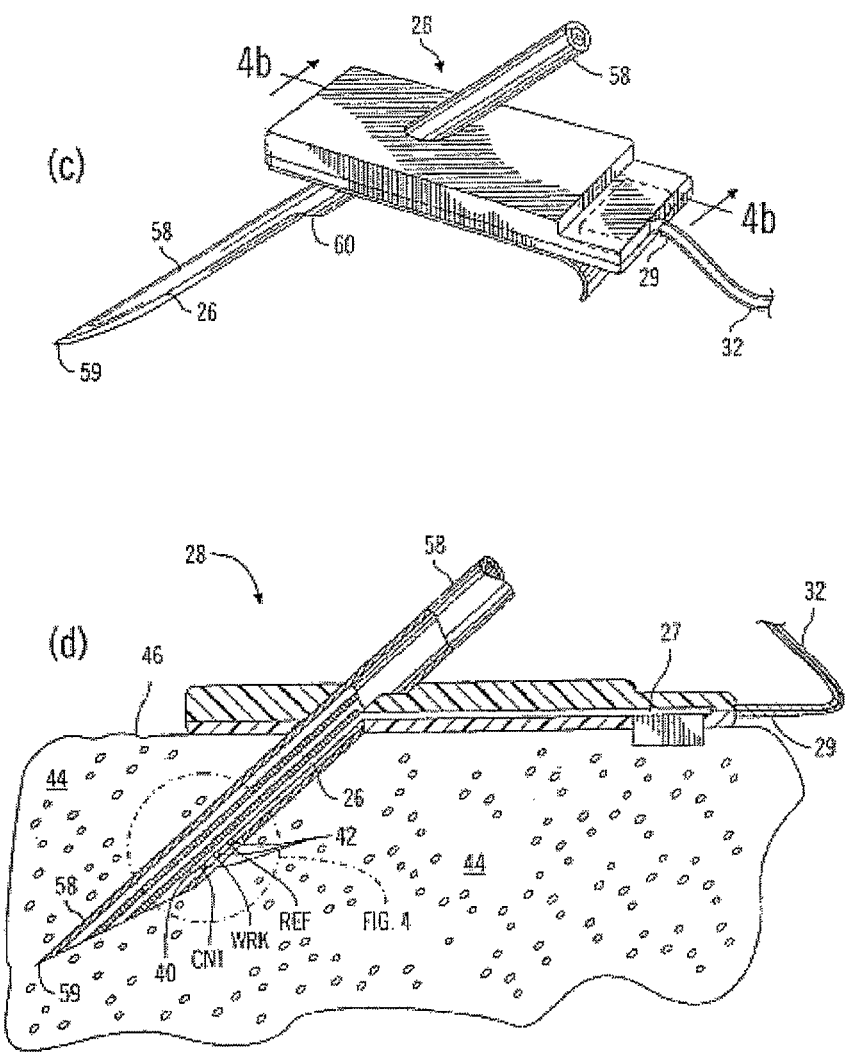
Figure 4:
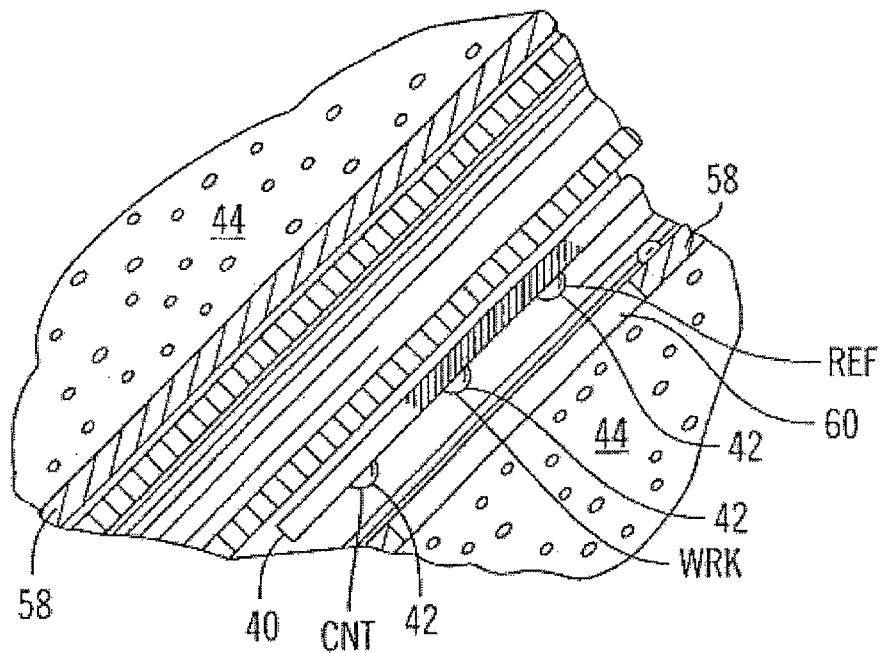
FIG. 4 is a cross sectional view of a sensing end of the sensor of FIG. 3(d).

Particular embodiments may include a sensor 26, a sensor set 28, a telemetered characteristic monitor 30, a sensor cable 32, an infusion device 34, an infusion tube 36, and an infusion set 38, all worn on the body 20 of a user or patient, as shown in FIG. 2. Telemetered characteristic monitor 30 includes a monitor housing 31 that supports a printed circuit board 33, batteries 35, antenna (not shown), and a sensor cable connector (not shown), as seen in FIGS. 3(a) and 3(b). A sensing end 40 of the sensor 26 has exposed electrodes 42 and is inserted through skin 46 into a subcutaneous tissue 44 of a user's body 20, as shown in FIGS. 3(d) and 4. Electrodes 42 are in contact with interstitial fluid (ISF) that is present throughout subcutaneous tissue 44. Sensor 26 is held in place by sensor set 28, which is adhesively secured to the user's skin 46, as shown in FIGS. 3(c) and 3(d). Sensor set 28 provides for a connector end 27 of sensor 26 to connect to a first end 29 of sensor cable 32. A second end 37 of sensor cable 32 connects to monitor housing 31. Batteries 35 included in monitor housing 31 provide power for sensor 26 and electrical components 39 on printed circuit board 33. Electrical components 39-sample sensor signal 16 and store digital sensor values (Dsig) in a memory and then periodically transmit the digital sensor values Dsig from the memory to controller 12, which is included in the infusion device.

Figure 5:
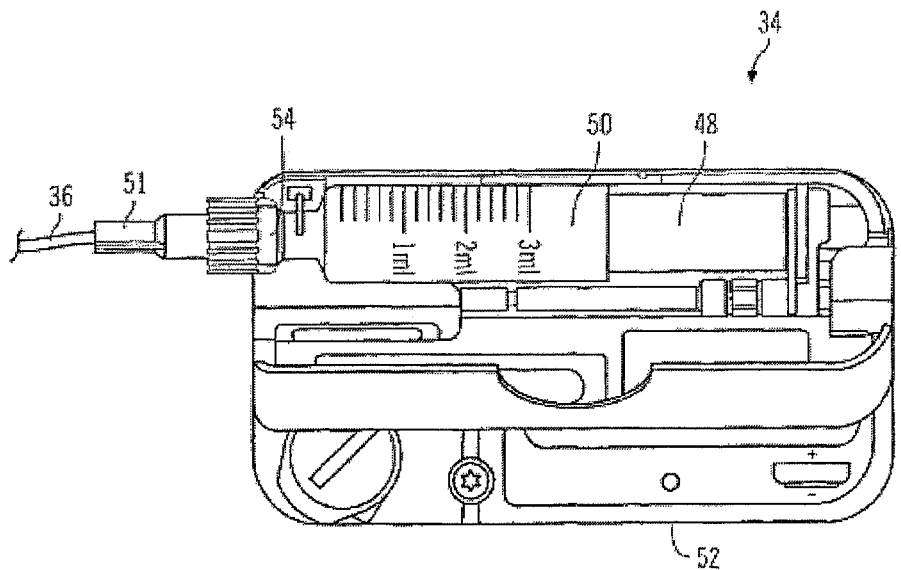
FIG. 5 is a top view of an infusion device with a reservoir door in the open position, for use according to an embodiment.
Figure 6:
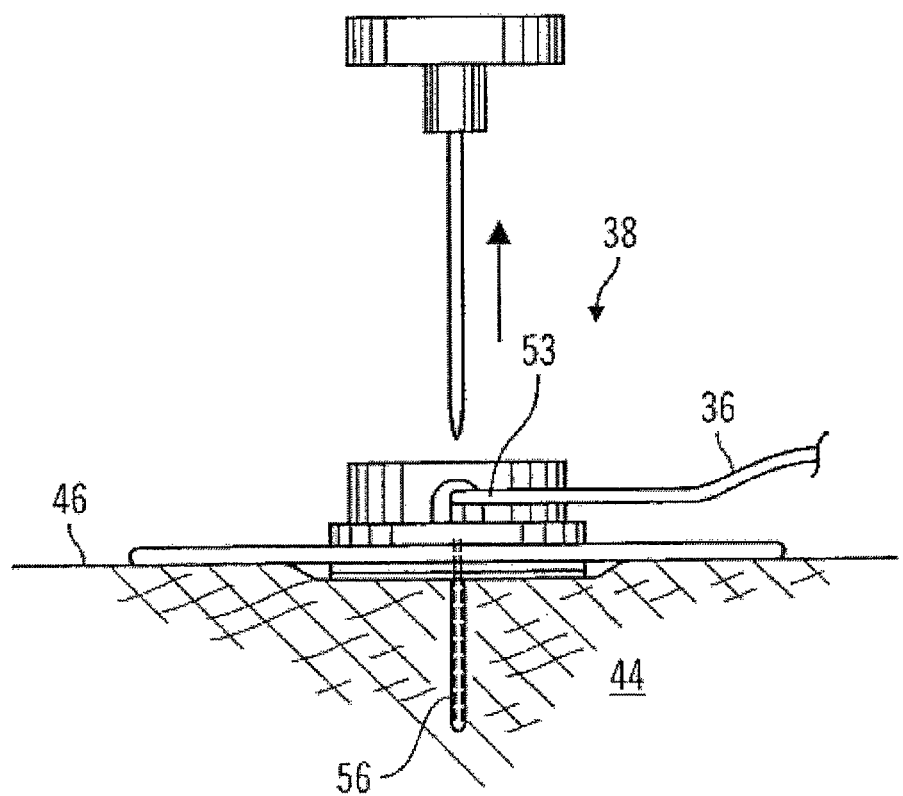
FIG. 6 is a side view of an infusion set with the insertion needle pulled out, for use in an embodiment.
Figure 7:
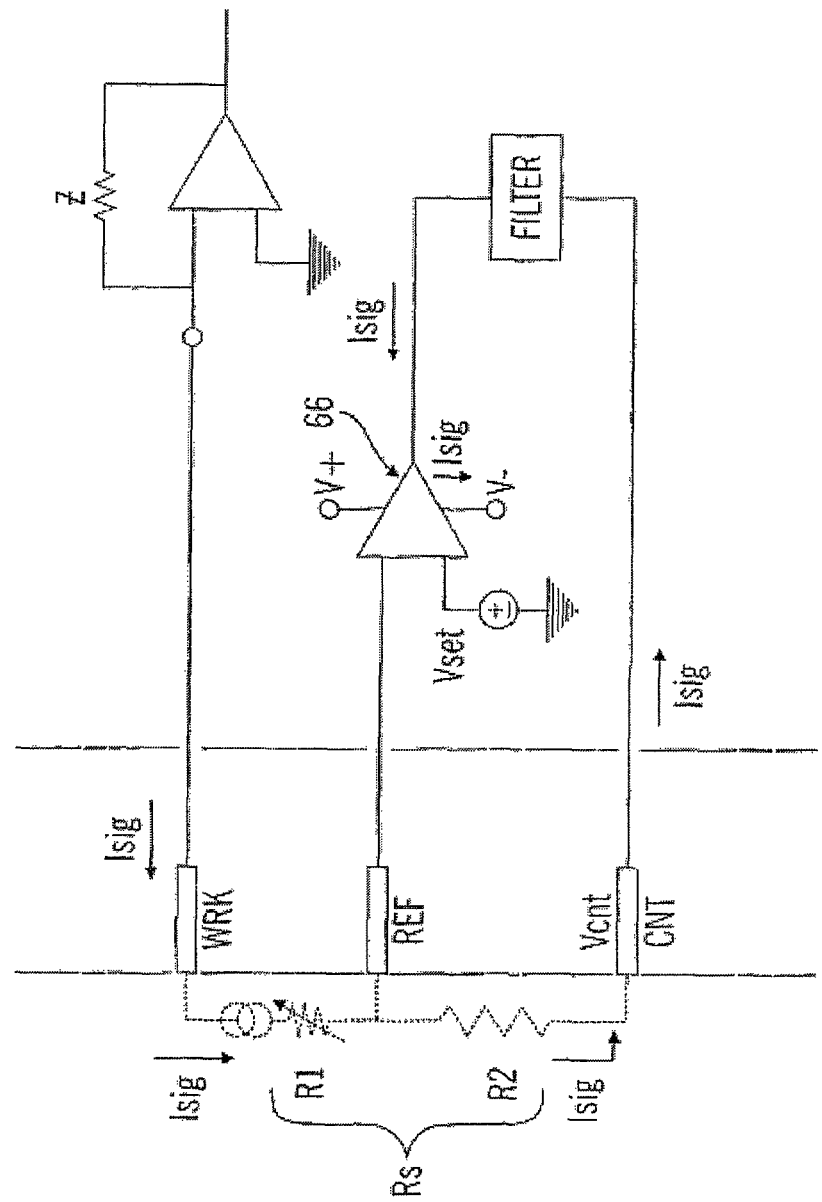
FIG. 7 is a circuit diagram of a sensor and its power supply in accordance with an embodiment.

Controller 12 processes the digital sensor values Dsig and generates commands 22 for infusion device 34. Infusion device 34 may respond to commands 22 and actuate a plunger 48 that forces insulin 24 out of a reservoir 50 located inside the infusion device 34, as shown in FIG. 5. In particular embodiments, a connector tip 54 of reservoir 50 extends through infusion device housing 52 and a first end 51 of infusion tube 36 is attached to connector tip 54. A second end 53 of infusion tube 36 connects to infusion set 38. Insulin 24 is forced through infusion tube 36 into infusion set 38 and into body 16. Infusion set 38 is adhesively attached to the user's skin 46, as shown in FIG. 6. As part of infusion set 38, a cannula 56 extends through skin 46 and terminates in subcutaneous tissue 44 completing fluid communication between the reservoir 50 and subcutaneous tissue 44 of the user's body 16.

In alternative embodiments, the closed-loop system can be a part of a hospital-based glucose management system. Given that insulin therapy during intensive care has been shown to dramatically improve wound healing, reduce blood stream infections, renal failure, and polyneuropathy mortality, irrespective of whether subjects previously had diabetes (See Van den Berghe G. et al. NEJM 345: 1359-67, 2001), particular implementations can be used in a hospital setting to control the blood glucose level of a patient in intensive care. In these alternative embodiments, since an intravenous (IV) hookup may be implanted into a patient's arm while the patient is in an intensive care setting (e.g., ICU), a closed loop glucose control can be established which piggy-backs off the existing IV connection. Thus, in a hospital based system, IV catheters which are directly connected to a patient vascular system for purposes of quickly delivering IV fluids, can also be used to facilitate blood sampling and direct infusion of substances (e.g. insulin, anticoagulants) into the intra-vascular space. Moreover, glucose sensors may be inserted through the IV line to give real-time glucose levels from the blood stream. Therefore, depending on the type of hospital-based system, the alternative embodiments would not necessarily need the described system components such as the sensor 26, the sensor set 28, the telemetered characteristic monitor 30, the sensor cable 32, the infusion tube 36, and the infusion set 38—Instead, standard blood glucose meters or vascular glucose sensors as described in co-pending U.S. patent application Ser. No. 12/121,647, filed May 15, 2008, can be used to provide the blood glucose values to the infusion pump control and the existing IV connection can be used to administer the insulin to the patient.

It is important to appreciate that numerous combinations of devices in the hospital-based system can be used with a closed loop controller as described herein. For example, an auto blood glucose/intravenous insulin infusion system can automatically withdraw and analyze blood for glucose concentration at fixed intervals (e.g., 5-20 minutes), extrapolate blood glucose values at a more frequent interval (e.g., one minute), and use the extrapolated signal for calculating an IV-insulin infusion according to a controller.

In still further alternative embodiments, system components may be combined in a smaller or greater number of devices and/or the functions of each device may be allocated differently to suit the needs of the user.

Controller

Once hardware for a closed loop system is configured, as described above, the effects of the hardware on a human body are determined by the controller. In particular embodiments, controller 12 is designed to model a pancreatic beta cell (β-cell). In other words, controller 12 commands infusion device 34 to release insulin 24 into body 20 at a rate that causes the insulin concentration in the blood to follow a similar concentration profile as would be caused by fully functioning human β-cells responding to blood glucose concentrations in the body 20.

A controller that simulates the body's natural insulin response to blood glucose levels not only makes efficient use of insulin but also accounts for other bodily functions as well since insulin has both metabolic and mitogenic effects. Controller algorithms that are designed to minimize glucose excursions in the body without regard for how much insulin is delivered may cause excessive weight gain, hypertension, and atherosclerosis. In particular embodiments, controller 22 is intended to emulate the in vivo insulin secretion pattern and to adjust this pattern to be consistent with in vivo β-cell adaptation. The in vivo β-cell response in subjects with normal glucose tolerance (NGT), with widely varying insulin sensitivity (SI), is the optimal insulin response for the maintenance of glucose homeostasis.

System Configurations

The following sections provide exemplary, but not limiting, illustrations of components that may be utilized with the controller described above. Various changes in components, layout of various components, combinations of elements, or the like may be made without departing from the scope of claims subject matter.

Figure 8:
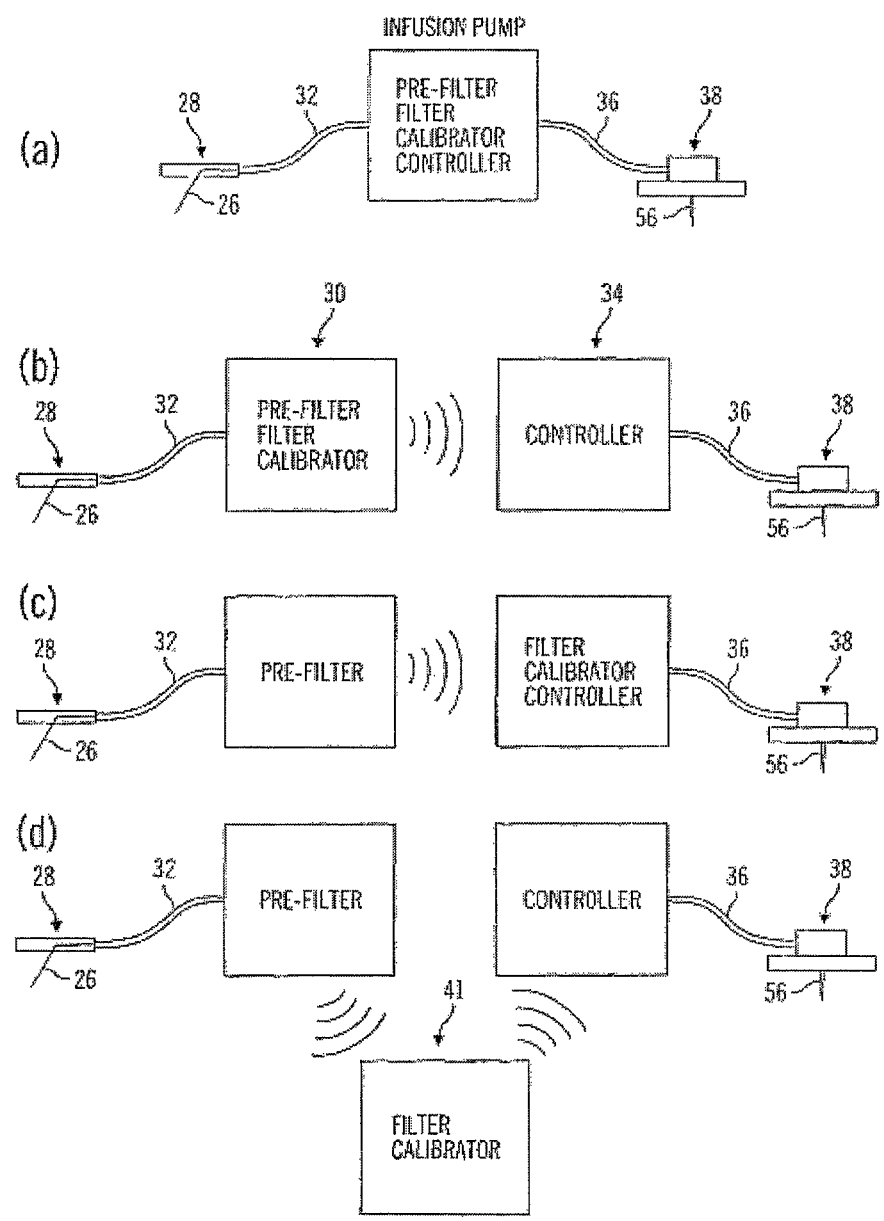
FIG. 8(a) is a diagram of a single device and its components in accordance with an embodiment.
FIG. 8(b) is a diagram of two devices and their components in accordance with an embodiment.
FIG. 8(c) is another diagram of two devices and their components in accordance with an embodiment.
FIG. 8(d) is a diagram of three devices and their components in accordance with an embodiment.

Before it is provided as an input to controller 12, sensor signal 16 may be subjected to signal conditioning such as pre-filtering, filtering, calibrating, and/or the like. Components such as a pre-filter, one or more filters, a calibrator, and the controller 12 may be separately partitioned or physically located together, and may be included with a telemetered characteristic monitor transmitter 30, infusion device 34, or a supplemental device. In particular embodiments, pre-filter, filters and the calibrator are included as part of telemetered characteristic monitor transmitter 30, and controller 20 is included with infusion device 34, as shown in FIG. 8(b). In alternative embodiments, a pre-filter may be included with telemetered characteristic monitor transmitter 30 and a filter and calibrator may be included with controller 12 in an infusion device, as shown in FIG. 8(c). In other alternative embodiments, a pre-filter may be included with telemetered characteristic monitor transmitter 30, while the filter and calibrator are included in supplemental device 41, and the controller is included in the infusion device, as shown in FIG. 8(d).

In particular embodiments, a sensor system generates a message that includes information based on the sensor signal such as digital sensor values, pre-filtered digital sensor values, filtered digital sensor values, calibrated digital sensor values, commands, or the like. Such a message may include other types of information as well such as a serial number, an ID code, a check value, values for other sensed parameters, diagnostic signals, other signals, or the like. In particular embodiments, the digital sensor values Dsig may be filtered in the telemetered characteristic monitor transmitter 30, and then the filtered digital sensor values may be included in the message sent to the infusion device 34 where the filtered digital sensor values are calibrated and used in the controller. In other embodiments, the digital sensor values Dsig may be filtered and calibrated before transmission to the controller 12 in infusion device 34. Alternatively, the digital sensor values Dsig may be filtered, and calibrated and used in the controller to generate commands 22 that are then sent from the telemetered characteristic monitor transmitter 30 to infusion device 34.

In further embodiments, additional optional components, such as a post-calibration filter, a display, a recorder, and a blood glucose meter may be included in the devices with any of the other components or they may stand-alone. Here, if a blood glucose meter is built into one of the devices, it may be co-located in the device that contains the calibrator. In alternative embodiments, one or more of the components are not used.

In particular embodiments, RF telemetry is used to communicate between devices, such as telemetered characteristic monitor transmitter 30 and the infusion device 34, which contain groups of components. In alternative embodiments, other communication mediums may be employed between devices such as wires, cables, IR signals, laser signals, fiber optics, ultrasonic signals, or the like.

Filtering

In particular embodiments, the digital sensor values Dsig and/or the derivative of the digital sensor values are processed, filtered, modified, analyzed, smoothed, combined, averaged, clipped, scaled, calibrated, or the like, to minimize the effects of anomalous data points before they are provided as an input to the controller. In particular embodiments, the digital sensor values Dsig are passed through a pre-filter 400 and then a filter 402 before they are passed to the transmitter 70, as shown in FIG. 15. The filters are used to detect and minimize the effects of anomalous digital sensor values Dsig. Some causes of anomalous digital sensor values Dsig may include temporary signal transients caused by sensor separation from the subcutaneous tissue, sensor noise, power supply noise, temporary disconnects or shorts, and/or the like. In particular embodiments, each individual digital sensor value Dsig is compared to maximum and minimum value-thresholds. In other particular embodiments, the differences between consecutive pairs of digital sensor values Dsig are compared with rate-of-change-thresholds for increasing or decreasing values.

Pre-Filter

In particular embodiments, the pre-filter 400 uses fuzzy logic to determine whether individual digital sensor values Dsig need to be adjusted. The pre-filter 400 uses a subset of a group of digital sensor values Dsig to calculate a parameter and then uses the parameter to determine whether individual digital sensor values Dsig need to be adjusted in comparison to the group as a whole. For example, the average of a subset of a group of digital sensor values Dsig may be calculated, and then noise thresholds may be placed above and below the average. Then individual digital sensor values Dsig within the group are compared to noise thresholds and eliminated or modified if they are outside of the noise thresholds.

Figure 16:
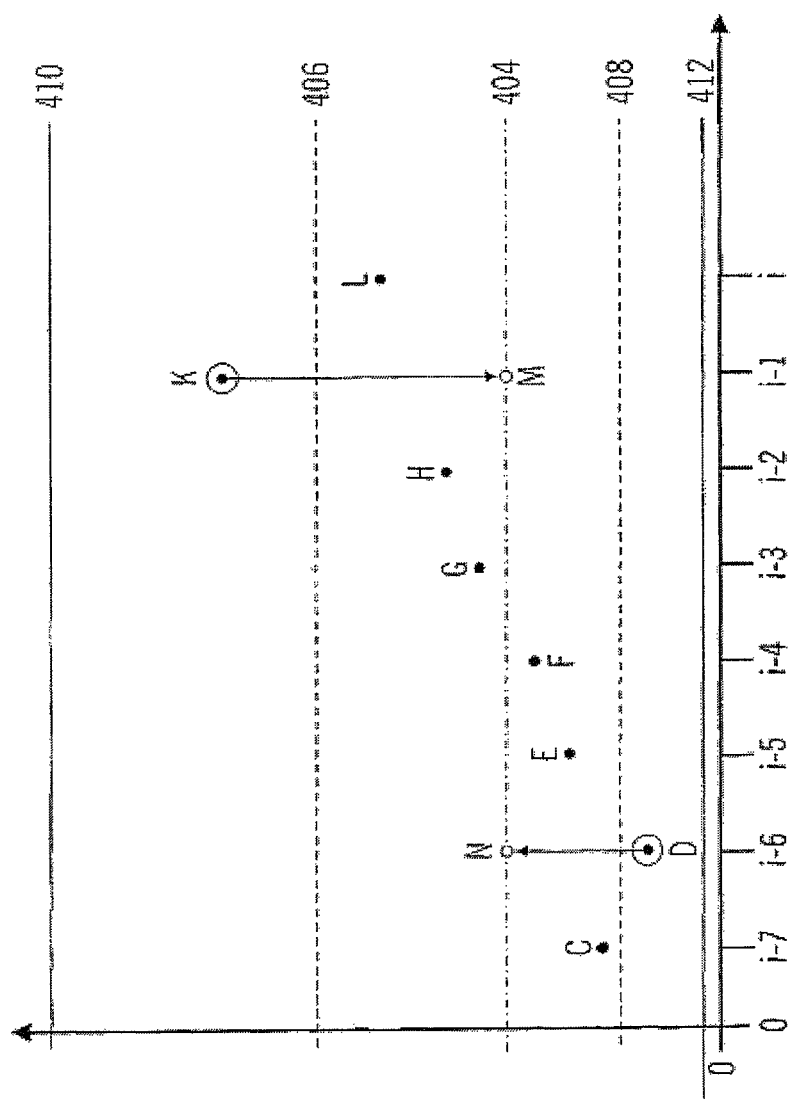
FIG. 16 is a chart of an example of a pre-filter of FIG. 16 and its effects on digital sensor values Dsig in accordance with an embodiment.

A more detailed example is provided below to more clearly illustrate, but not limit, an embodiment of a pre-filter. A group of eight digital sensor values Dsig are shown in FIG. 16 including a most recently sampled value, labeled L, sampled from the analog sensor signal Isig at time i, and the seven previous values K, H, G, F, E, D, and C sampled at times (i-1) through (i-7). An average value is calculated using the four temporally middle values in the group, H, G, F, and E sampled at times (i-2) through (i-5). The calculated average value is represented as a dashed/dotted average line 404. A high noise threshold 406 is established at 100% above the average line 404. In other words, the magnitude of the high noise threshold 406 is two times the magnitude of the average line 404. A negative noise threshold 408 is established at 50% below the average line 404. In other words, the magnitude of the negative noise threshold 408 is one-half of the magnitude of the average line 404. The individual magnitudes of each of the eight values, L, K, H, G, F, E, D, and C are compared to the high and negative noise thresholds 406 and 408. If a value is above the high noise threshold 406 or below the negative noise threshold 408 then the value is considered anomalous and the anomalous value is replaced with the magnitude of the average line 404. In the example shown in FIG. 16, the value K is above the high noise threshold 406 so it is replaced with the average value M. Also, the value D is below the negative noise threshold 408 so it is replaced with the average value N. In this way noisy signal spikes are reduced. Therefore, in the example, values L, K, H, G, F, E, D, and C are inputs to the pre-filter 400 and values L, M, H, G, F, E, N, and C are outputs from the pre-filter 400. In alternative embodiments, other noise threshold levels (or percentages) may be used. In other alternative embodiments, values outside of the thresholds may be replaced with values other than the average value, such as the previous value, the value of the closest threshold, a value calculated by extrapolating a trend line through previous data, a value that is calculated by interpolation between other values that are inside the thresholds, or the like.

In particular embodiments, if any of a group's values are outside of the noise thresholds 406 or 408 then a warning flag may be set. If one to three values are outside of the noise thresholds 406 or 408, a 'noise' flag may be set. If more than three values are outside of the noise thresholds 406 or 408, a 'discard' flag may be set which indicates that the whole group of values should be ignored and not used. In alternative embodiments, more or less values need be outside of the thresholds 406 or 408 to trigger the 'noise' flag or the 'discard' flag.

In particular embodiments, each digital sensor value Dsig may be checked for saturation and disconnection. To continue with the example of FIG. 16, each individual value is compared to a saturation threshold 410. If a value is equal to or above the saturation threshold 410 then a 'saturation' flag is set. In particular embodiments, if the 'saturation' flag is set, a warning may be provided to the user that the sensor 26 may need calibration or replacement. In further particular embodiments, if an individual digital sensor value Dsig is at or above saturation threshold 410, individual digital sensor value Dsig may be ignored, changed to a value equal to average line 404, or the entire group of values associated with the individual digital sensor value Dsig may be ignored. In particular embodiments, saturation threshold 410 may be set at about 16% below a maximum value of the range of digital sensor values that may be generated. In particular embodiments, a maximum digital sensor value represents a glucose concentration greater than 150 mg/dl. In alternative embodiments, a maximum digital sensor value may represent larger or smaller a glucose concentrations depending on a range of expected glucose concentrations to be measured, sensor accuracy, sensor system resolution needed for a particular application (e.g., closed loop control), and/or the like. The full range of values is the difference between the maximum and the minimum digital sensor value that may be generated. Higher or lower saturation threshold levels may be used depending on an expected signal range of the sensor, sensor noise, sensor gains, or the like.

Similarly, in particular embodiments, if a digital signal value Dsig is below a disconnect threshold 412, then a 'disconnect' flag may be set indicating to a user that the sensor is not properly connected to the power supply and that the power supply or sensor may need replacement or recalibration. In further particular embodiments, if a digital sensor value Dsig is below the disconnect threshold 412, the individual value may be ignored, changed to a value equal to the average line 404, or the entire group of values associated with the individual digital sensor value Dsig may be ignored. In particular embodiments, disconnect threshold 410 may be set at about 20% of the full range of values. Higher or lower disconnect threshold levels may be used depending on an expected signal range of the sensor, sensor system noise, sensor gains, or the like.

In alternative embodiments, other methods may be used to pre-filter the digital sensor values Dsig such as rate-of-change thresholds, rate-of-change squared thresholds, noise thresholds about a least squares fit line rather than about the average of a subset of a group's values, higher or lower noise threshold lines, or the like.

Noise Filter

After the digital sensor values Dsig are evaluated, and if necessary, modified by the pre-filter 400, the digital sensor values Dsig are passed to the filter 402. The filter 402 may be used to reduce noise in particular frequency bands. A body's blood glucose level 18 may change relatively slowly compared to a rate at which digital sensor values Dsig are collected. Therefore, high frequency signal components may comprise noise, and a low pass filter may be used to improve the signal to noise ratio.

Figure 17:
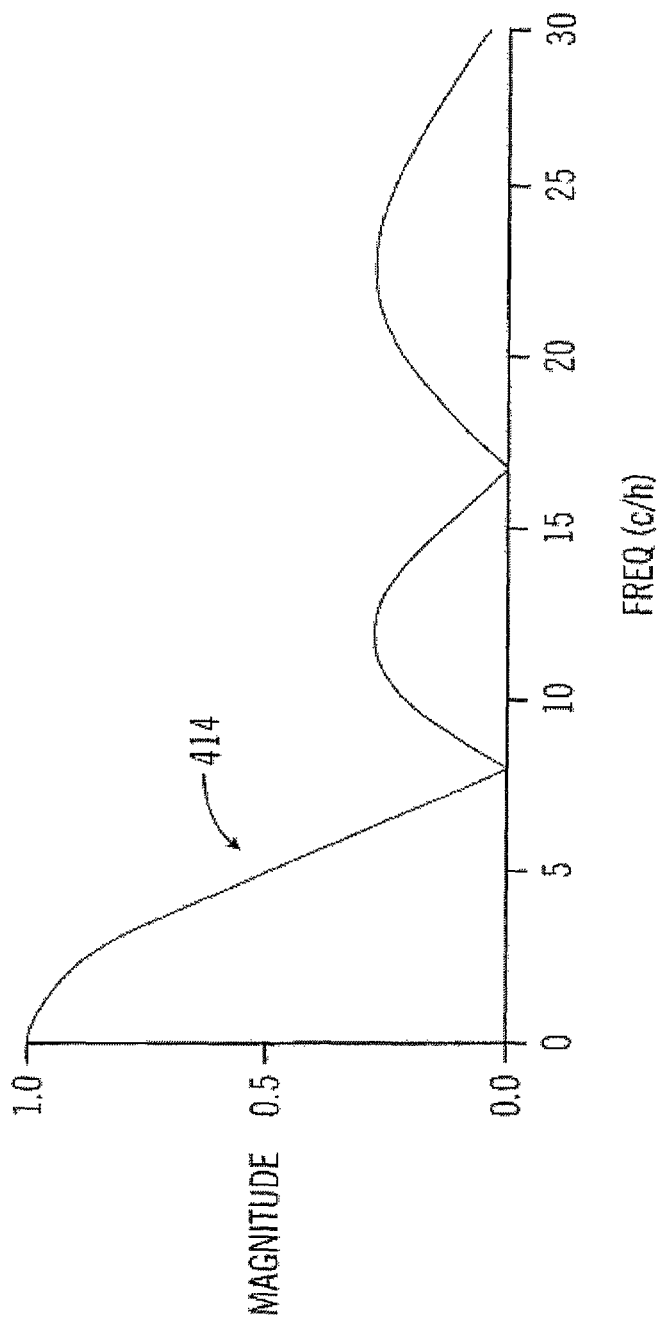
FIG. 17 illustrates a frequency response for a filter of FIG. 16 in accordance with an embodiment.
Figure 18:
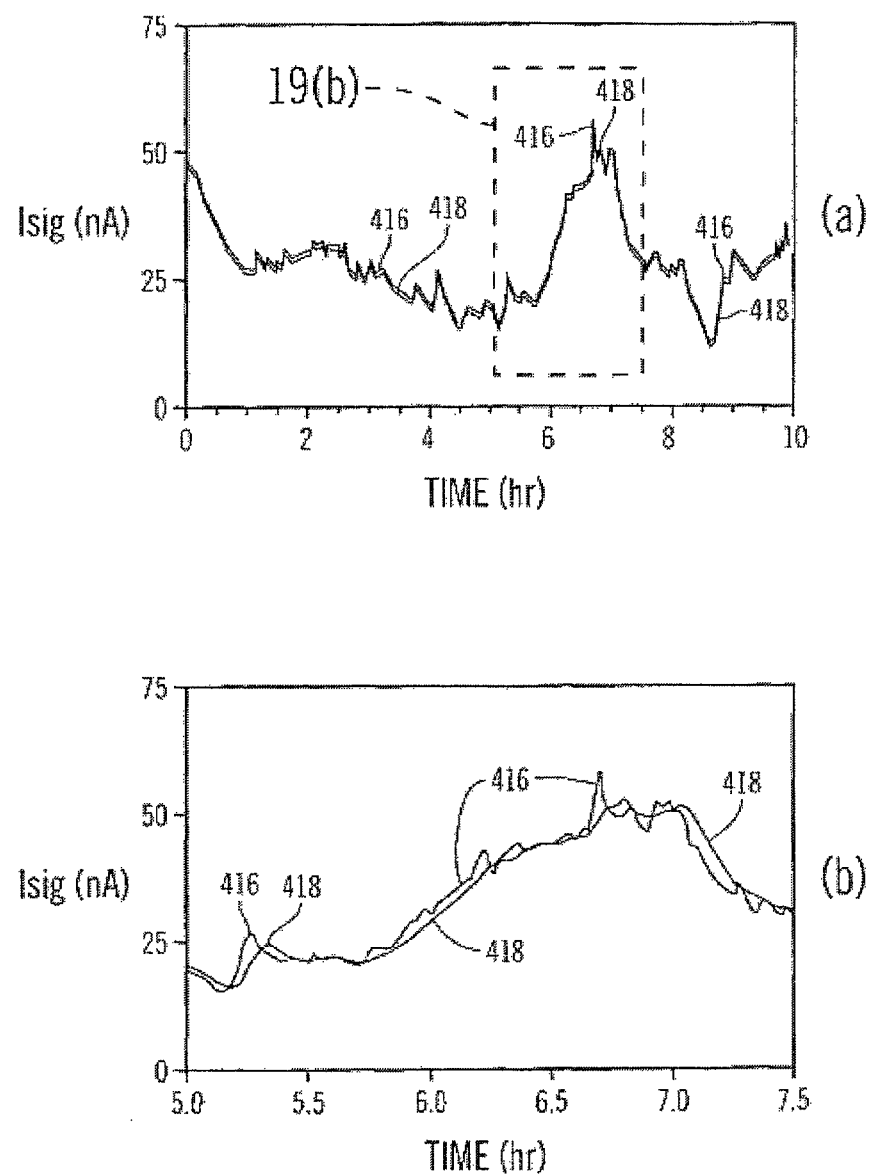
FIG. 18(a) is a plot of a filtered and an unfiltered sensor signal over time in accordance with an embodiment.
FIG. 18(b) is close up of a section of the plot of FIG. 19(a) in accordance with an embodiment.

In particular embodiments, filter 402 may comprise a finite impulse response (FIR) filter used to reduce noise. In particular embodiments, such a FIR filter is a 7th order filter tuned with a pass band for frequencies from zero to three cycles per hour (c/hr) and a stop band for frequencies greater than about 6 c/hr, as shown in an example frequency response curve 414 in FIG. 17. However, typically FIR filters tuned with a pass band for frequencies from zero up to between about 2 c/hr and 5 c/hr and a stop band beginning at 1.2 to three times the selected pass band frequency will sufficiently reduce noise while passing the sensor signal. In particular embodiments, FIR filters tuned with a pass band for frequencies from zero up to between about 2 c/hr and 10 c/hr and a stop band beginning at 1.2 to three times the selected pass band frequency may sufficiently reduce noise. In the 7th order filter, unique weighting factors may be applied to each of eight digital sensor values Dsig. Digital sensor values Dsig may include the most recently sampled value and the seven previous values. Effects of a low pass filter on a digital sensor values collected at one minute intervals is shown in FIGS. 18(a) and (b). An unfiltered sensor signal curve 416 of digital sensor values is contrasted with a curve of the same signal after the effects of a 7th order FIR filter 418. Filtered signal curve 418 is delayed and the peaks are smoother compared to the unfiltered sensor signal curve 416. In other particular embodiments, higher or lower order filters may be used. In still other particular embodiments, filter weighting coefficients may be applied to digital sensor values Dsig collected at time intervals shorter or longer than one minute depending on the desired sensor sample rate based on the body's physiology, the computational capabilities of the telemetered characteristic monitor transmitter 30, the sensor's response time, or the like. In alternative embodiments, filters with other frequency responses may be used to eliminate other noise frequencies depending on the type of sensor, noise from the power supply or other electronics, the sensor's interaction with the body, the effects of body motion on the sensor signal, or the like. In still other alternative embodiments, the filter comprises an infinite impulse response (IIR) filter.

Figure 19:
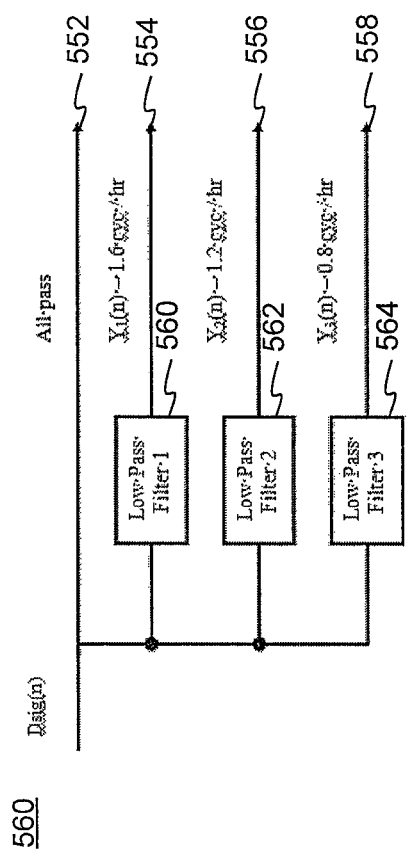
FIG. 19 is a schematic diagram of a digital filter topology for concurrently processing a sensor signal in multiple filter-signal paths according to an embodiment.

As discussed above, in particular embodiments, a filter (such as filter 402) may comprise multiple filter-signal paths for providing an associated plurality of candidate output signals. Again, one of the candidate output signals may then be selected based, at least in part, on a measurement of noise associated with sensor signal 16. As shown in FIG. 19 according to a particular implementation, such a selectable filtering scheme 550 may comprise four filter-signal paths 552, 554, 556 and 558. Here, the digital signal Dsig may be represented as the signal Dsig(n). The signal Dsig(n) may comprise an $n^{th}$ digital sample obtained from pre-filter 400. Here, Dsig(n) may be concurrently processed by three distinct filters on associated filter-signal paths 554, 556 and 558. Filter-signal path 552 comprises an all pass filter or provides no filtering. Accordingly, filtering scheme 550 offers a selection of a signal from among four filter output signals based, at least in part, on a measurement of noise associated with Dsig(n).

Figure 21:
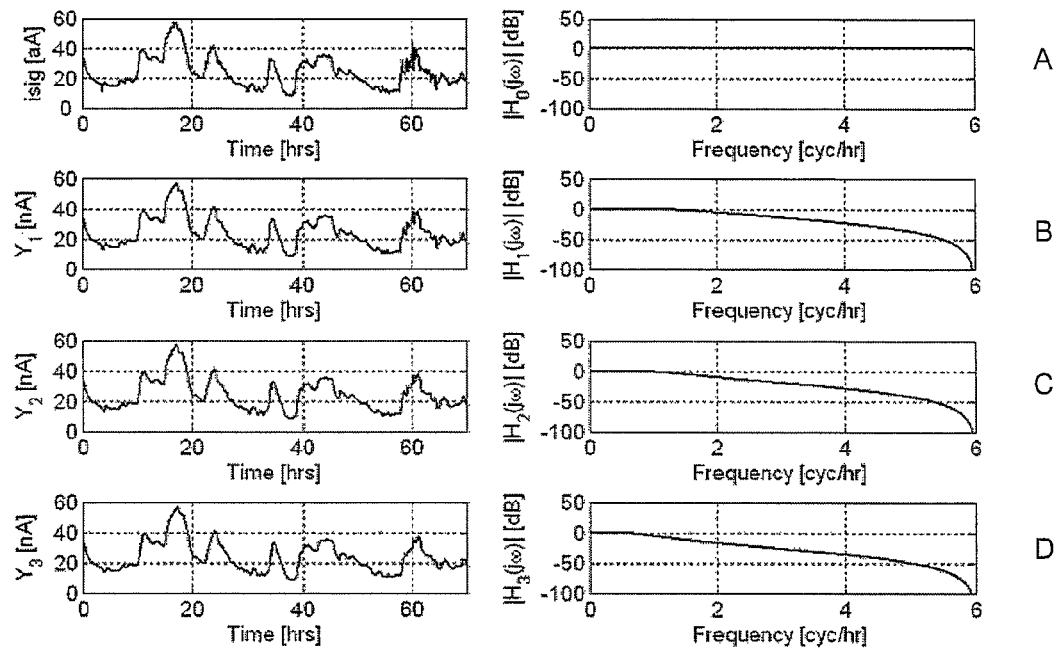
FIG. 21A-21D are plots of transfer functions and associated filtered sensor signals for a plurality of filter-signal paths.

According to a particular embodiment, frequency responses of filter-signal paths 552, 554, 556 and 558 are shown on the right-hand side of FIGS. 21A, 21B, and 21C, respectively. Corresponding filtered output signals are shown in the left-hand side of FIGS. 21A, 21B, and 21C, respectively. Low pass filters 560, 562, and 564 for providing these frequency responses may be implemented using any one of several digital filters such as FIR or IIR filters as discussed above. In other embodiments, adaptive filters or Kalman filters may be used. It should be understood, however, that these are merely examples of different types of digital filters that may be used and that claimed subject matter is not limited in this respect. In this particular example, the continuous signal isig is sampled at five-minute intervals, providing a Nyquist frequency of 6.0 cycles/hour. Filter outputs Y1, Y2, and Y3, corresponding to respective filter-signal paths 554, 556, and 558, have cut-off frequencies of 1.6, 1.2 and 0.8 cycles/hour, respectively. An increasing level of artifact reduction can be shown at time t>58.0 hours for each filter residual, where noise appears relatively high.

As discussed below, at any point in time, a particular filter-signal path may be dynamically selected from among filter-signal paths 552, 554, 556 and 558 for providing an output signal based, at least in part, on a measurement of noise associated with isig. Accordingly, filter output signals may be selected from a filter-signal path applying more robust filtering (and with an associated group delay) while isig is obtained in the presence of high noise. Conversely, filter output signals may be selected from a filter-signal path applying less robust filtering (and with less of a group delay) while isig is obtained in the presence of lower noise.

Figure 20:
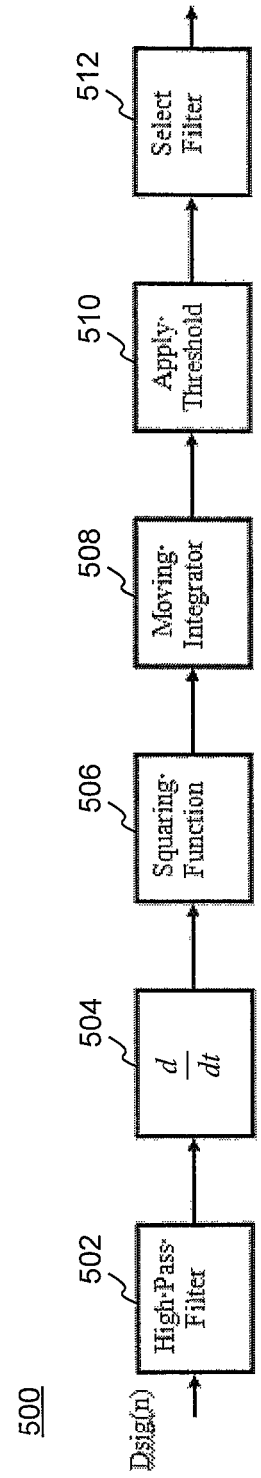
FIG. 20 is a schematic diagram of a system for measuring noise associated with a sensor signal according to an embodiment.
Figure 22:
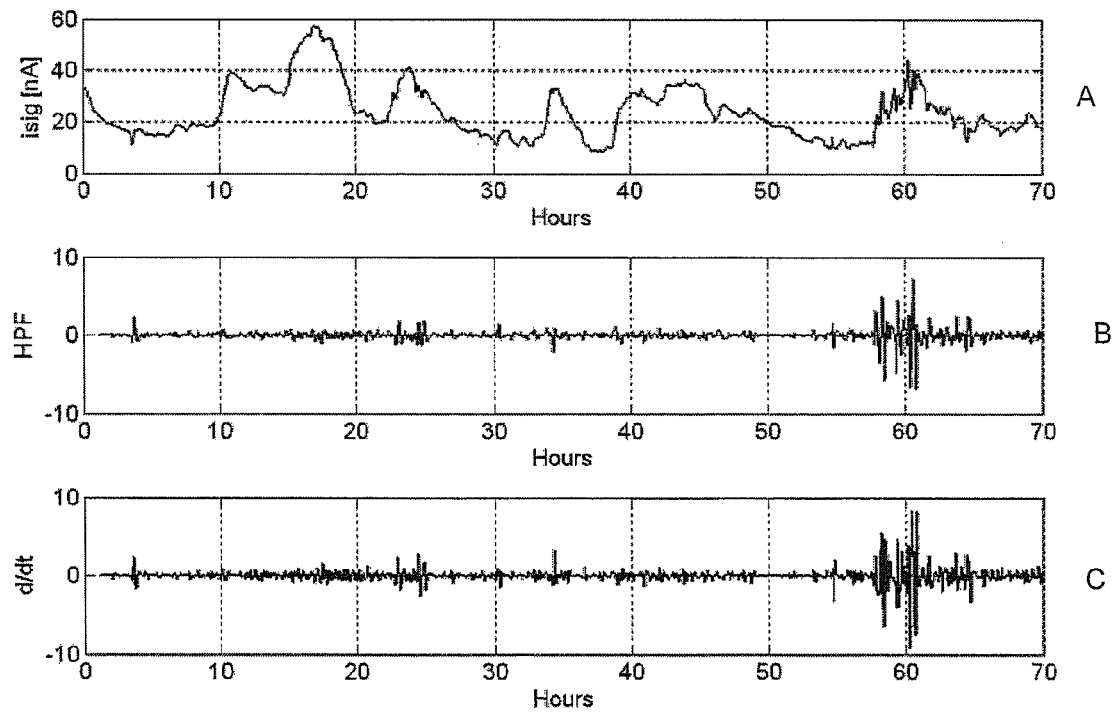
FIGS. 22A-22C and 23A-23C are plots of a sensor signal as processed for measuring noise associated with the sensor signal according to an embodiment.

FIG. 20 illustrates a process for measuring noise associated with sensor signal 16. As pointed out above in one embodiment, the value Dsig(n) may comprise an $n^{th}$ digital sample obtained from pre-filter 400. However, the value Dsig(n) may comprise a digitized sensor signal from any one of several points in filter processing downstream from A/D converter 68. A first trace of FIG. 22A shows an example of un-processed signal Dsig(n) over a seventy-hour interval. In this particular example, samples of the sensor signal are obtained at five-minute intervals and generally have amplitudes of less than 100 nA. Here, such a signal is roughly proportional to blood-glucose concentration. In particular implementations, Dsig(n) may be calibrated using reference blood glucose measurements using techniques described in U.S. Pat. Nos. 6,895,263 and 6,424,847. The signal Dsig(n) over the aforementioned seventy-hour period appears relatively smooth until time t>58.0 hours where high amplitude interference appears.

To quantify noise associated with a sensor signal, high pass filter 502 may remove a portion of the desired blood-glucose signal, and substantially retain only noise and artifact components of isig(n). In a particular implementation, a second order IIR filter with a cut-off frequency of 2.0 cyc/hour and about a delay of six minutes may be used to separate blood-glucose from noise and artifact components. A resulting trace for the output of high pass filter 502 for a particular implementation is shown in the trace of FIG. 22B. It should be understood, however, that different types of high pass filter arrangements may be used. A derivative function 504 is applied to the isolated noise and artifact components to obtain slope information and/or measure how frequently these components are changing. Here, a first order derivative may be applied to enable faster real-time noise detection. A resulting trace for the output of derivative function 504 in a particular implementation is shown in FIG. 22C.

Figure 23:
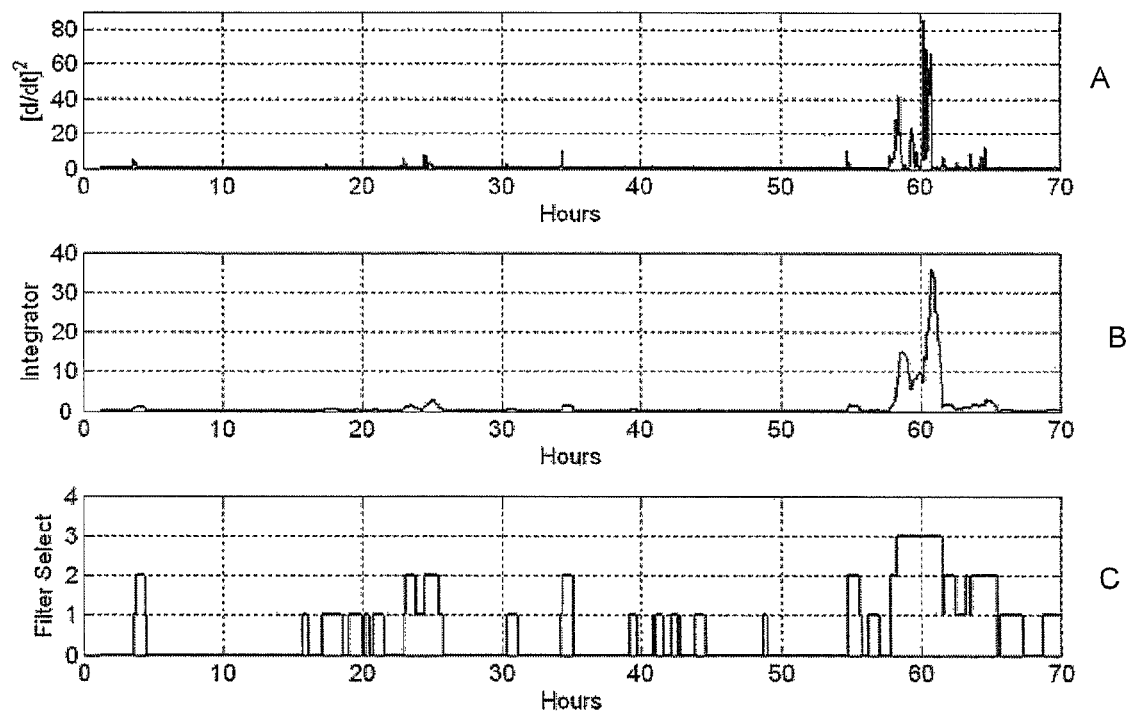

Block 506 performs a squaring function to make sample points positive and provide a nonlinear amplification emphasizing higher frequencies. A resulting trace for the output of block 506 according to an embodiment is shown in FIG. 23A. Block 508 applies a moving integration window to the squared sample points to extract additional information by averaging a set number of samples (or time interval) within a given window length. A resulting trace for the output of block 508 according to an embodiment is shown in FIG. 23B. In one particular implementation, a ten sample moving average length spanning a 50-minute interval may be used. However, this is merely an example of such a duration for a moving integration window and claimed subject matter is not limited in this respect. Block 510 applies a threshold detection of the result of block 508 to map the result to one of a plurality of discrete levels or values. Here, as shown in FIG. 23C for a particular implementation, the result of block 508 is mapped to one of four discrete levels. Of course, such a result may be mapped to one of a different number of discrete levels. A particular filtering scheme is then selected at block 512 based upon the mapped level.

In a particular implementation, although claimed subject matter is not limited in this respect, discrete levels determined at block 510 may correspond with dynamic selection of an output signal from among filter-signal paths 552, 554, 556 and 558. For example, as shown in of FIG. 23C, an output signal may be selected from filter-signal path 552 in a lowest-noise environment while measured noise from block 510 maps to level 0. Similarly, an output signal may be selected from filter-signal path 558 while measured noise from block 510 maps to level 3. Likewise, an output signal may be selected from filter-signal path 554 while measured noise from block 510 maps to level 1, or selected from filter-signal path 556 while measured noise from block 510 maps to level 2.

Figure 24:
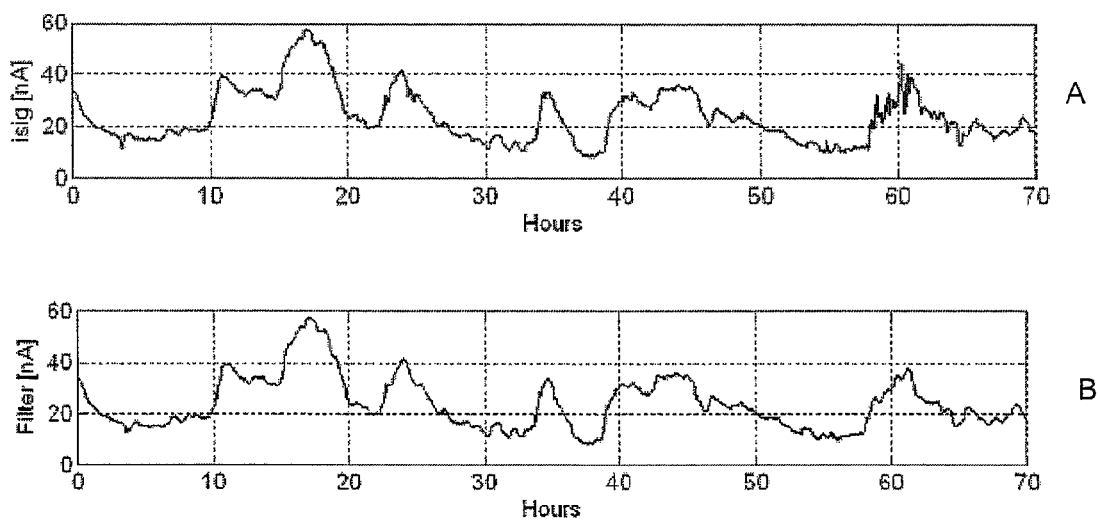
FIG. 24A is a plot of an un-filtered sensor signal.
FIG. 24B is a plot of a sensor signal filtered by different filter-signal paths at different time intervals according to an embodiment.

FIGS. 24A and 24B show a particular example of dynamic selection of a filter-signal path to provide an output signal based, at least in part, on a measurement of noise associated with the signal Dsig(n). Here, the trace of FIG. 24A shows the signal isig while the lower trace shows a filtered output. As can be observed from of FIG. 23C, an output signal may be selected from filter-signal path 552, providing an all-pass or no filtering, in the interval 5 h<t<15 h. Accordingly, the resulting output in period 5 h<t<15 h as shown in FIG. 24B is identical to isig(n) during this period. In contrast, an output signal may be selected from filter-signal path 558, providing the most robust filtering, in the interval 58 h<t<61 h. Here, the resulting output in this period as shown in the lower trace of FIG. 23B removes much of the artifacts in Dsig(n) during this period as shown in the upper trace of FIG. 23A.

Delay Compensation Filter

Aside from noise reduction, a filter may used to compensate for time delays. Ideally, a sensor would provide a real time, noise-free measurement of a parameter that a control system is intended to control, such as a blood glucose measurement. However, realistically there are physiological, chemical, electrical, and algorithmic sources of time delays that cause the sensor measurement to lag behind the present value of blood glucose. Also, as pointed out above, such a delay may arise from a particular level of noise filtering applied to a sensor signal.

Figure 25:
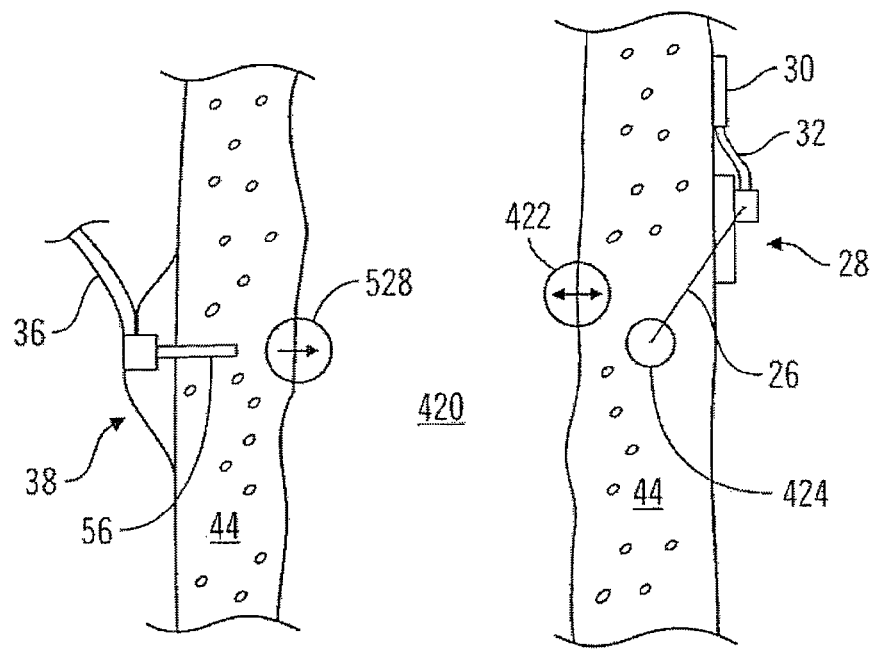
FIG. 25 is a cross-sectional view of a sensor set and an infusion set attached to the body in accordance with an embodiment.

In a particular implementation, as shown in FIG. 25, a physiological delay may arise from the time required for glucose to move between blood plasma 420 and interstitial fluid (ISF). The delay is represented by the circled double-headed arrow 422 in FIG. 25. As discussed above, sensor 26 may be inserted into the subcutaneous tissue 44 of the body 20 and electrodes 42 near the tip of sensor 40 are in contact with interstitial fluid (ISF). But a desired parameter to be measured includes a concentration of blood glucose. Glucose is carried throughout the body in blood plasma 420. Through the process of diffusion, glucose may move from the blood plasma 420 into the ISF of subcutaneous tissue 44 and vice versa. As blood glucose level 18 changes so does the glucose level in the ISF. But the glucose level in the ISF may lag behind the blood glucose level 18 due to the time required for the body to achieve glucose concentration equilibrium between the blood plasma 420 and the ISF. Studies show the glucose lag times between blood plasma 420 and ISF may vary between 0.0 to 30.0 minutes. Some parameters that may affect such a glucose lag time between blood plasma 420 and ISF are the individual's metabolism, the current blood glucose level, whether the glucose level is rising, or falling, or the like.

A chemical reaction delay 424 may be introduced by the sensor response time, represented by the circle 424 surrounding the tip of the sensor 26 in FIG. 25. The sensor electrodes 42 are coated with protective membranes that keep the electrodes 42 wetted with ISF, attenuate the glucose concentration, and reduce glucose concentration fluctuations on the electrode surface. As glucose levels change, the protective membranes slow the rate of glucose exchange between the ISF and the electrode surface. In addition, there is a chemical reaction delay simply due to the reaction time for glucose to react with glucose oxidase GOX to generate hydrogen peroxide, and the reaction time for a secondary reaction, the reduction of hydrogen peroxide to water, oxygen and free electrons.

As discussed above, there may also be a processing delay as the analog sensor signal Isig is converted to digital sensor values Dsig. In particular embodiments, an analog sensor signal Isig may be integrated over one-minute intervals and then converted to a number of counts. In essence an A/D conversion time may result in an average delay of 30 seconds. In particular embodiments, the one-minute values may be averaged into 5-minute values before they are sent to the controller. A resulting average delay is then two and one half minutes. In alternative embodiments, longer or shorter integration times may be used resulting in longer or shorter delay times. In other embodiments the analog sensor signal current Isig is continuously converted to an analog voltage Vsig and a A/D converter samples the voltage Vsig every 10 seconds. Then six 10-second values are pre-filtered and averaged to create a one-minute value. Finally, five 1-minute values may be filtered and then averaged creating a five-minute value resulting in an average delay of two and one half minutes. Other embodiments use other electrical components or other sampling rates and result in other delay periods.

Again, as pointed out above, filters may also introduce a delay due to the time required to acquire a sufficient number of digital sensor values Dsig to operate a digital filter. Higher order filters, by definition, require more digital sensor values Dsig. Aside from the most recent digital sensor value Dsig, FIR filters use a number of previous values equal to the order of the filter. For example, a 7th order filter uses 8 digital sensor values Dsig. There is a time interval between each digital sensor value Dsig. To continue with the example, if the time interval between digital sensor values Dsig is one minute, then the oldest digital sensor value Dsig used in a 7th order FIR filter would be seven minutes old. Therefore, the average time delay for all of the values used in the filter is three and a half minutes. However, if the weighting factors associated with each of the values are not equal then the time delay may be longer or shorter than three and one half minutes depending on the effects of the coefficients.

Figure 26:
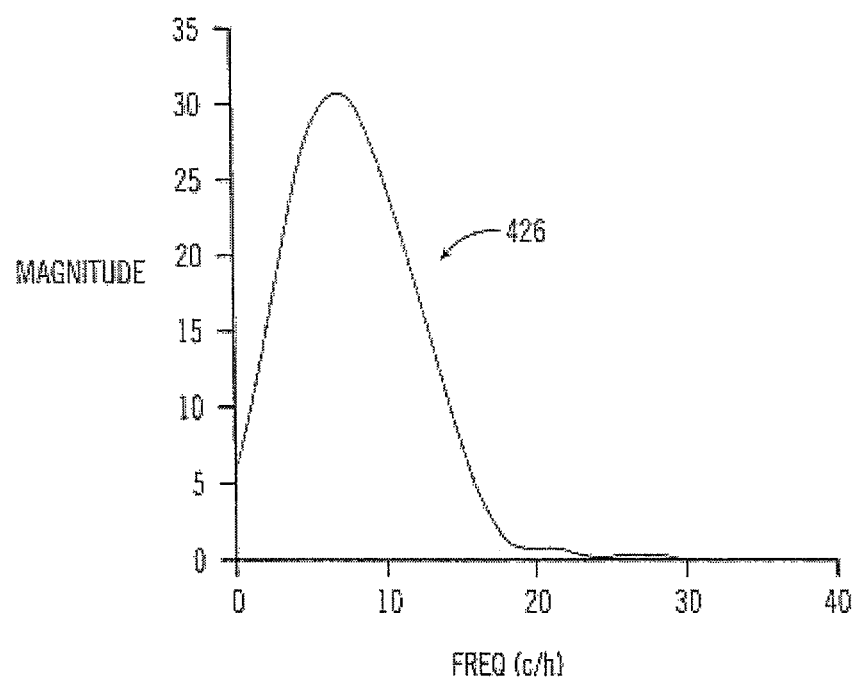
FIG. 26 is a frequency response chart of a time delay correcting Weiner filter in accordance with an embodiment.

Particular embodiments may include a FIR filter that compensates for both the various time delays, of up to about 30 minutes as discussed above, and high frequency noise, greater than about 10 c/hr also discussed above. Particular embodiments employ a $7^{th}$ order Weiner type FIR filter. The coefficients for the filter are selected to correct for time lags while simultaneously reducing high frequency noise. An example of a frequency response curve 426 is shown in FIG. 26. The example frequency response curve 416 is generated for a Weiner filter with a pass band for frequencies from zero up to about 8 c/hr and a stop band for frequencies greater than about 15 c/hr for a sensor with a sensitivity of about 20 µA/100 mg/dl.

In alternative embodiments, other types of filters may be used. In other alternative embodiments, no time compensation is used if a rate of change in the blood glucose level is slow compared to the time delay. For example, a five-minute delay between blood plasma glucose and a sensor measurement does not have to be corrected for a closed loop glucose control system to function.

Calibration

In particular embodiments, after filtering, digital sensor values Dsig may be calibrated with respect to one or more glucose reference values. Such glucose reference values may be entered into a calibrator for comparison with digital sensor values Dsig. Such a calibrator may apply a calibration algorithm to convert the digital sensor values Dsig, which may be in counts into blood glucose values. In particular embodiments, the calibration method is of the type described in U.S. Pat. No. 6,424,847 or 6,895,263. In particular embodiments, a calibrator may be included as part of the infusion device 34 and glucose reference values may be entered by the user into the infusion device 34. In other embodiments, glucose reference values may be entered into the telemetered characteristic monitor transmitter 30 while a calibrator calibrates the digital sensor values Dsig and transmits calibrated digital sensor values to infusion device 34. In further embodiments, glucose reference values may be entered into a supplemental device where calibration is executed. In alternative embodiments, a blood glucose meter is in communication with the infusion device 34, telemetered characteristic monitor transmitter 30 or supplemental device so that glucose reference values may be transmitted directly into device that the blood glucose meter may be in communication with. In additional alternative embodiments, a blood glucose meter is part of the infusion device 34, telemetered characteristic monitor transmitter 30 or supplemental device such as that shown in U.S. patent application Ser. No. 09/334,996, filed on Jun. 17, 1999, entitled "CHARACTERISTIC MONITOR WITH A CHARACTERISTIC METER AND METHOD OF USING THE SAME".

In particular embodiments, to obtain blood glucose reference values, one or more blood samples may be extracted from body 20, and a common, over-the-counter, blood glucose meter may be used to measure blood plasma glucose concentration of the samples. Then a digital sensor value Dsig may be compared to the blood glucose measurement from the meter and a mathematical correction is applied to convert the digital sensor values Dsig to blood glucose values. In alternative embodiments, a solution of a known glucose concentration is introduced into the subcutaneous tissue surrounding the sensor 26 by using methods and apparatus such as described in U.S. Pat. No. 6,254,586, or by using injection, infusion, jet pressure, introduction through a lumen, or the like. A digital sensor value Dsig is collected while the sensor 26 is bathed in the solution of known glucose concentration. A mathematical formula such as a factor, an offset, an equation, or the like, is derived to convert the digital sensor value Dsig to the known glucose concentration. A mathematical formula is then applied to subsequent digital sensors values Dsig to obtain blood glucose values. In alternative embodiments, the digital sensor values Dsig may be calibrated before filtering. In additional alternative embodiments, the digital sensor values Dsig may be calibrated after pre-filtering and before filtering. In other alternative embodiments, sensors are calibrated before they are used in the body or do not require calibration at all.

Sensor Signal Processing Systems

Figure 9:
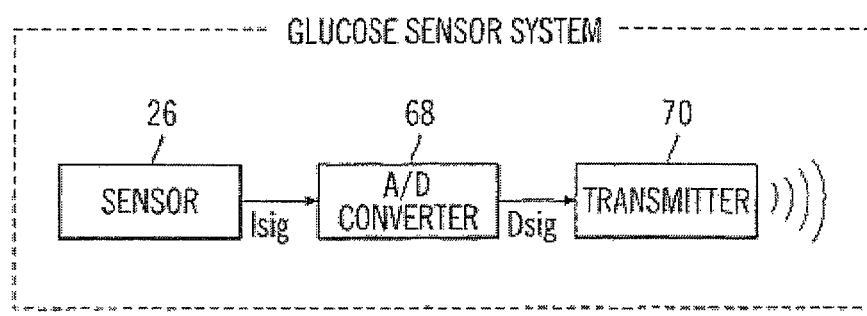
FIG. 9 is a block diagram of a glucose sensor system according to an embodiment.
Figure 10:
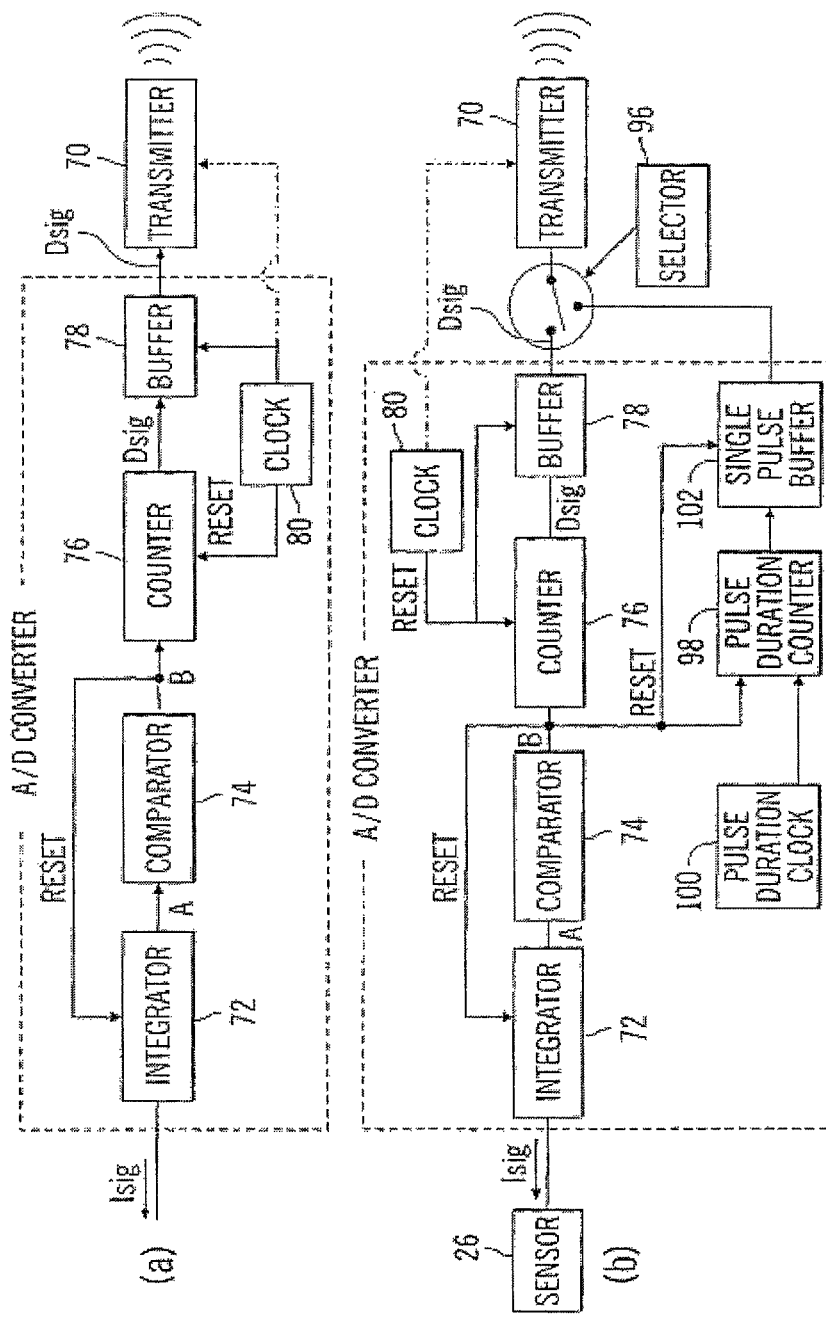
FIG. 10(a) is a schematic block diagram of an A/D converter for the glucose sensor system of FIG. 9 in accordance with an embodiment.
FIG. 10(b) is a schematic block diagram of the A/D converter for the glucose sensor system of FIG. 9 with a pulse duration output selection option in accordance with an embodiment.

Before filtering and calibrating, generally the sensor signal is processed to convert the sensor signal from a raw form into a form acceptable for use in the filters and/or calibrator. In particular embodiments, as shown in FIG. 9, an analog sensor signal Isig is digitally quantified through an A/D converter 68 resulting in digital sensor values Dsig that are transmitted by a transmitter 70 from the telemetered characteristic monitor transmitter 30 to another device. In particular embodiments, the analog sensor signal Isig is an analog current value that is converted to a digital sensor value Dsig in the form of a digital frequency measurement, as shown in FIG. 10(*a*). Here, such circuitry may include an integrator 72, a comparator 74, a counter 76, a buffer 78, a clock 80, and the transmitter 70. The integrator 72 generates a substantially ramped voltage signal (A), and the instantaneous slope of the ramped voltage signal is proportional to the magnitude of the instantaneous analog sensor signal Isig. Comparator 74 converts the ramped voltage signal (A) from the integrator 72 into square wave pulses (B). Pulses from the comparator 74 increment counter 76 and also reset integrator 72. Clock 80 periodically triggers buffer 78 to store a present value from counter 76, and then reset counter 76. Values stored in buffer 78 include the digital sensor values Dsig. Clock 80 may also periodically signal transmitter 70 to send a value from buffer 78. In particular embodiments, a clock period is one minute. However, in alternative embodiments, such a clock period may be adjusted based on how often measurements are needed, sensor signal noise, sensor sensitivity, desired measurement resolution, the type of signal to be transmitted, or the like. In alternative embodiments, a buffer is not used.

A/D Converters

Various A/D converter designs may be used in particular embodiments. The following examples are illustrative, and not limiting, since other A/D converters may be used.

I to F (Current to Frequency (Counts)), Single Capacitor, Quick Discharge

Figure 11:
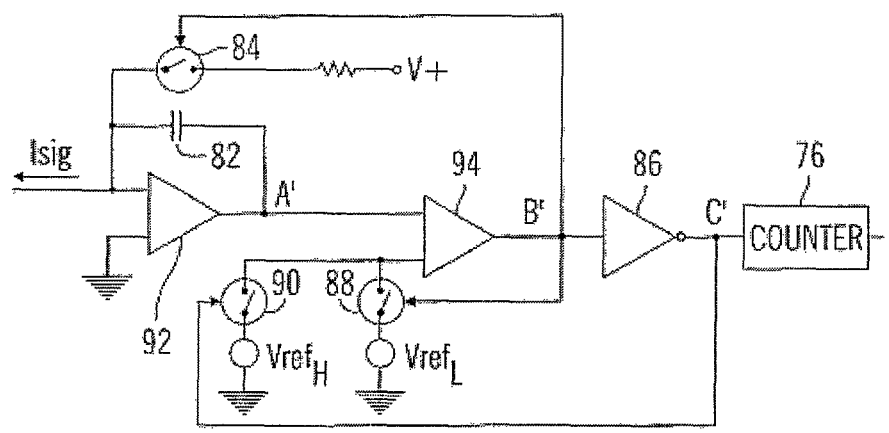
FIG. 11 is a circuit diagram of an I-F A/D converter of FIG. 9 accompanied by charts of node signals in accordance with an embodiment.
Figure 11:
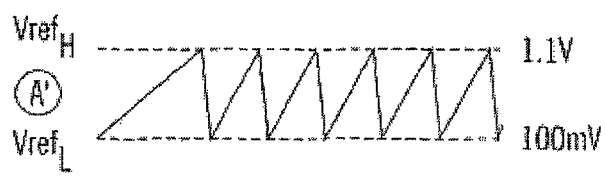
Figure 11:
Figure 11:
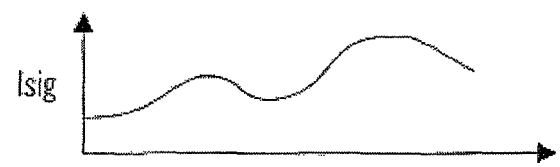

In particular embodiments, integrator 72 consists of a first Op-Amp 92 and a capacitor 82, shown in FIG. 11. Integrator 72 sums the analog sensor signal Isig current by charging the capacitor 82 until the capacitor voltage (A') achieves a high reference voltage ($Vref_H$). Capacitor voltage (A') is measured at the output of first Op-Amp 92. A second Op-Amp 94 is used as a comparator. If the capacitor voltage (A') reaches $Vref_H$, the comparator output (B') changes from low to high. The high comparator output (B') closes a reset switch 84 that discharges capacitor 82 through a voltage source (V+). High comparator output (B') also triggers a reference voltage switch 88 to close, while substantially simultaneously an inverter 86 inverts the comparator output (B'). And the inverter output ((C')) triggers a reference voltage switch 90 to open. The result is that the reference voltage of the comparator is changed from $Vref_H$ to the low reference voltage ($Vref_L$).

When the capacitor voltage (A') is discharged to $Vref_L$, the comparator output (B') returns to low, thus forming a pulse. The low comparator output (B') opens the reset switch 84 allowing the capacitor 82 to begin charging again.

Virtually simultaneously, the low comparator output (B') may also triggers the reference voltage switch 88 to open and the inverter output ((C')) may trigger reference voltage switch 90 to close resulting in changing the comparator reference voltage from $Vref_L$ back to $Vref_H$.

I to F, Single Reversible Capacitor

In alternative embodiments, two or more integrator switches may be used to control the polarity of one or more capacitors. A particular embodiment is shown in FIG. 12. Here, only one of the two integrator-switches 110 and 112 may be closed and the other integrator switch is open. If the first integrator switch 110 is closed, second integrator switch 112 may be open and an integrator Op-Amp 114 may sum the analog sensor signal Isig current by charging a capacitor 116 until the capacitor voltage (A") achieves a high reference voltage ($Vref_H$). Comparator 120 may compare integrator output (A") to reference voltage $Vref_H$. If the capacitor voltage (A") reaches $Vref_H$, the comparator output (B") shifts from low to high, initiating a pulse.

High comparator output (B") pulse may cause the capacitor polarity to reverse using the following method. High comparator output (B") triggers the second integrator switch 112 to close while virtually simultaneously inverter 118 inverts comparator output (B"). And the low inverter output ((C")) pulse triggers first integrator switch 110 to open. Once the capacitor's polarity is reversed, capacitor 116 discharges at a rate proportional to the analog sensor signal Isig. The high comparator output (B") pulse also triggers the reference voltage of the comparator to change from $Vref_H$ the low reference voltage ($Vref_L$). When the capacitor voltage (A") is discharged to $Vref_L$, the comparator output (B") returns to low. The low comparator output (B") may open the second integrator switch 112 and virtually simultaneously the high inverter output ((C")) closes the first integrator switch 110 allowing capacitor 116 to begin charging again. The low comparator output (B") also triggers the comparator reference voltage to change from $Vref_L$ back to $Vref_H$.

An advantage of this embodiment is that sensor signal errors, which may be created due to capacitor discharge time, are reduced since the magnitude of the analog sensor signal Isig drives both the charging and the discharging rates of the capacitor 116.

I to F, Dual Capacitor

In further alternative embodiments, more than one capacitor is used such that as one capacitor is charging, at a rate proportional to the magnitude of the analog sensor signal Isig, another capacitor is discharging. An example of this embodiment is shown in FIG. 13. A series of three switches are used for each capacitor. A first group of switches 210 is controlled by a latch voltage C''', and a second group of switches 212 are controlled by voltage D''', which is the inverse of C'''. Substantially, only one group of switches is closed at a time. If the first group of switches 210 is closed, the voltage across a first capacitor 216 increases at a rate proportional to the analog sensor signal Isig until the integrator voltage (A''') at the output of Op-Amp 214 achieves a reference voltage (Vref). At the same time one of the switches shorts the circuit across a second capacitor 222 causing it to discharge. A comparator 220 compares the integrator output (A''') to the reference voltage Vref. As the integrator output (A''') reaches Vref, the comparator output (B''') generates a pulse. The comparator output pulse increments a counter 76, and triggers the latch output voltage C''' from a latch 221 to toggle from a low voltage to a high voltage. The change in the latch voltage C''' causes the second group of switches 212 to close and the first group of switches 210 to open. One of the switches from the second group of switches 212 shorts the circuit across the first capacitor 216 causing it to discharge. At the same time the voltage across the second capacitor 222 increases at a rate proportional to the analog sensor signal Isig until the integrator voltage (A''') at the output of Op-Amp 214 achieves a reference voltage (Vref). Again, the comparator 220 compares the integrator output (A''') to the reference voltage Vref. And when the integrator output (A''') reaches Vref, the comparator output (B''') generates a pulse. The comparator output pulse increments the counter 76, and triggers the latch output voltage C''' to toggle from a high voltage to a low voltage, which causes the switches to return to their initial position with the first group of switches 210 closed and the second group of switches 212 to open.

In summary, as blood glucose level 18 increases, the analog sensor signal Isig increases, which causes the voltage coming out of integrator 72 to ramp up faster to the high reference voltage $Vref_H$, which causes comparator 74 to generate pulses more often, which adds counts to counter 76 faster. Therefore, higher blood glucose levels generate more counts per minute.

The charge storage capacity for the capacitors used in integrator 72, and the reference voltages $Vref_H$, and $Vref_L$ may be selected such that the count resolution for counts collected in a one-minute period at a glucose level of 200 mg/dl represents a blood glucose measurement error of less than 1 mg/dl. In particular embodiments, $Vref_H$ is 1.1 volts and $Vref_L$ is 0.1 volts. Higher or lower reference voltages may be selected based on the magnitude of the analog sensor signal Isig, the capacity of the capacitors, and the desired measurement resolution. The source voltage V+ is set to a voltage sufficiently high to discharge one or more capacitors quickly enough that the discharge times do not significantly reduce the number of counts per minute at a blood glucose level of 200 mg/dl.

Pulse Duration Output Feature

In particular embodiments, transmitter 70 transmits digital sensor values Dsig from buffer 78 whenever triggered by clock 80. However, in particular embodiments, the user or another individual may use a selector 96 to choose other outputs to be transmitted from the transmitter 70, as shown in FIG. 10(b). In particular embodiments, selector 96 is in the form of a menu displayed on a screen that is accessed by the user or another individual by using buttons on the surface of telemetered characteristic monitor transmitter 30. In other embodiments, a dial selector, dedicated buttons, a touch screen, a signal transmitted to the telemetered characteristic monitor transmitter 30, or the like, may be used. Signals that may be selected to be transmitted, other than the digital sensor values Dsig, include, but are not limited to, a single pulse duration, digital sensor values before pre-filtering, digital sensor values after pre-filtering but before filtering, digital sensor values after filtering, or the like.

In particular embodiments, a pulse duration counter 98 counts clock pulses from a pulse duration clock 100 until pulse duration counter 98 is reset by a rising or falling edge of a pulse from comparator 74, as shown in FIG. 10(b). The accumulated count at the time that pulse duration counter 98 is reset represents the pulse duration for a portion of a single pulse from comparator 74. The accumulated count from the pulse duration counter 98 is stored in the single pulse buffer 102 if triggered by the reset signal. If an individual selects the single pulse output, transmitter 70 transmits the values from single pulse buffer 102. The pulse duration clock 100 period must be sufficiently shorter than the period between individual pulse edges from the comparator 74 given a high analog sensor signal Isig to have sufficient resolution to quantify different pulse durations from the comparator 74.

I to V (Current to Voltage), Voltage A/D

Alternative methods may be used to convert the analog sensor signal Isig from an analog current signal to a digital voltage signal. The analog sensor signal Isig is converted to an analog voltage Vsig using an Op Amp 302 and a resistor 304, as shown in FIG. 14. And then periodically a clock 308 triggers an A/D converter 306 to take a sample value from the analog voltage Vsig and convert it to a digital signal representing the magnitude of the voltage. The output values of the A/D converter 306 are digital sensor values Dsig. The digital sensor values Dsig are sent to a buffer 310 and then to the transmitter 70. In particular embodiments, resistor 304 may be adjusted to scale the Vsig to use a significant portion of the range of voltage A/D converter 306 depending on the sensor sensitivity, the maximum glucose concentration to be measured, the desired resolution from voltage A/D converter 306, or the like.

In alternative embodiments, a buffer 310 is not needed and the digital sensor values Dsig are sent from the A/D converter directly to the transmitter 70. In other alternative embodiments, the digital sensor values Dsig are processed, filtered, modified, analyzed, smoothed, combined, averaged, clipped, scaled, calibrated, or the like, before being sent to the transmitter 70. In preferred embodiments, the clock 308 triggers a measurement every 10 seconds. In alternative embodiments, the clock 308 runs faster or slower triggering measurements more or less frequently depending on how quickly the blood glucose level can change, the sensor sensitivity, how often new measurements are needed to control the delivery system 14, or the like.

Finally, in other alternative embodiments, other sensor signals from other types of sensors, as discussed in the section "Sensor and Sensor Set" below, are converted to digital sensor values Dsig if necessary before transmitting the digital sensor values Dsig to another device.

Unless specifically stated otherwise, as apparent from the following discussion, it is appreciated that throughout this specification discussions utilizing terms such as "processing", "computing", "calculating", "determining", "estimating", "selecting", "weighting", "identifying", "obtaining", "representing", "receiving", "transmitting", "storing", "analyzing", "creating", "contracting", "associating", "updating", or the like refer to the actions or processes that may be performed by a computing platform, such as a computer or a similar electronic computing device, that manipulates or transforms data represented as physical, electronic or magnetic quantities or other physical quantities within the computing platform's processors, memories, registers, or other information storage, transmission, reception or display devices. Accordingly, a computing platform refers to a system or a device that includes the ability to process or store data in the form of signals. Thus, a computing platform, in this context, may comprise hardware, software, firmware or any combinations thereof. Further, unless specifically stated otherwise, a process as described herein, with reference to flow diagrams or otherwise, may also be executed or controlled, in whole or in part, by a computing platform.

It should be noted that, although aspects of the above system, method, or process have been described in a particular order, the specific order is merely an example of a process and claimed subject matter is of course not limited to the order described. It should also be noted that the systems, methods, and processes described herein, may be capable of being performed by one or more computing platforms. In addition, the methods or processes described herein may be capable of being stored on a storage medium as one or more machine readable instructions, that if executed may enable a computing platform to perform one or more actions. "Storage medium" as referred to herein relates to media capable of storing information or instructions which may be operated on, or executed by, by one or more machines. For example, a storage medium may comprise one or more storage devices for storing machine-readable instructions or information. Such storage devices may comprise any one of several media types including, for example, magnetic, optical or semiconductor storage media. For further example, one or more computing platforms may be adapted to perform one or more of the processed or methods in accordance with claimed subject matter, such as the methods or processes described herein. However, these are merely examples relating to a storage medium and a computing platform and claimed subject matter is not limited in these respects.

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of appended claims, and equivalents thereof.

What is claimed is:

1. A method comprising:
   obtaining a sensor signal from a blood glucose sensor of a sensor component of an apparatus, the sensor signal being representative of a blood glucose concentration;
   mapping a measurement of noise associated with the sensor signal to one of three or more discrete levels or values;
   selecting an output signal for use in determining an estimate of the blood glucose concentration from among a plurality of distinct signal-filter paths arranged concurrently based, at least in part, on the one of three or more discrete levels or values;
   generating one or more commands for an insulin delivery component of the apparatus based, at least in part, on the estimate of the blood glucose concentration; and
   transmitting the generated one or more commands to the insulin delivery component to regulate a rate of fluid infusion into a body.

2. The method of claim 1, and further comprising:
   generating the sensor signal based upon a measurement of the blood glucose concentration; and
   obtaining the measurement of noise contemporaneous with obtaining the measurement of the blood glucose concentration.

3. The method of claim 1, wherein the plurality of distinct signal-filter paths comprises at least one signal-filter path with no filtering and at least one signal-filter path comprising a finite impulse response (FIR) filter.

4. The method of claim 3, and further comprising selecting the output signal from the at least one signal-filter path with no filtering responsive to the measurement of the noise not exceeding a threshold level.

5. The method of claim 1, and further comprising:
   high-pass filtering the sensor signal to provide an isolated noise component; and
   determining the measurement of noise based, at least in part, on the isolated noise component.

6. The method of claim 1, and further comprising receiving the sensor signal representative of the blood-glucose concentration from a blood-glucose sensor implanted in a patient.

7. The method of claim 1, and further comprising:
   selecting an output signal for use in estimating the blood glucose concentration from a different one of the plurality of distinct signal-filter paths based, at least in part, in a change in the measurement of noise.

8. The method of claim 1, wherein at least one of the plurality of distinct signal-filter paths comprises a seventh-order FIR filter.

9. The method of claim 1, wherein at least one of the plurality of distinct signal-filter paths comprises an infinite impulse response filter.

10. The method of claim 1, wherein at least one of the plurality of distinct signal-filter paths comprises a Kalman filter.

11. An apparatus comprising:
    means for providing a signal representative of a blood glucose concentration comprising at least one sensor;
    means for mapping a measurement of noise associated with the sensor signal to one of three or more discrete levels or values;
    means for selecting an output signal for use in estimating the blood glucose concentration from among a plurality of distinct signal-filter paths arranged concurrently based, at least in part, on the one of three or more discrete levels or values;
    means for generating one or more commands for at least one infusion device based, at least in part, on the estimate of the blood glucose concentration; and
    means for transmitting the generated one or more commands to the at least one infusion device to regulate a rate of fluid infusion into a body.

12. The apparatus method of claim 11, and further comprising:
    means for generating the sensor signal based upon a measurement of the blood glucose concentration; and
    means for obtaining the measurement of noise contemporaneous with obtaining the measurement of the blood glucose concentration.

13. The apparatus of claim 11, wherein the plurality of distinct signal-filter paths comprises at least one signal-filter path with no filtering and at least one signal-filter path comprising a finite impulse response (FIR) filter.

14. The apparatus of claim 13, and further comprising means for selecting the output signal from the at least one signal-filter path with no filtering if the measurement of the noise is below a threshold level.

15. The apparatus of claim 11, and further comprising:
    means for high-pass filtering the sensor signal to provide an isolated noise component; and
    means for determining the measurement of noise based, at least in part, on the isolated noise component.

16. The apparatus of claim 11, and further comprising means for receiving the sensor signal representative of the blood-glucose concentration from a blood-glucose sensor implanted in a patient.

17. The apparatus of claim 11, and further comprising:
means for selecting an output signal for use in estimating the blood glucose concentration from a different one of the plurality of distinct signal-filter paths based, at least in part, in a change in the measurement of noise.

18. An apparatus comprising:
a blood-glucose sensor to generate a sensor signal representative of a blood-glucose concentration in a patient; and
a controller adapted to:
map a measurement of noise associated with the sensor signal to one of three or more discrete levels or values;
select an output signal for use in estimating the blood glucose concentration from among a plurality of distinct signal-filter paths arranged concurrently based, at least in part, on the one of three or more discrete levels or values; and
generate one or more commands to be transmitted to an insulin delivery system to regulate a rate of fluid infusion into a body, the one or more commands to be based, at least in part, on the estimate of the blood glucose concentration.

19. The apparatus of claim 18, and further comprising the plurality of distinct filter-signal paths, the plurality of distinct filter-signal paths being adapted to concurrently process sensor signal to provide respective candidate output signals.

20. The apparatus of claim 19, wherein the plurality of distinct signal-filter paths comprises at least one signal-filter path with no filtering and at least one signal-filter path comprising a finite impulse response (FIR) filter.

21. The apparatus of claim 18, and further comprising:
a high-pass filter to provide an isolated noise component, and wherein the controller is adapted to determine the measurement of noise based, at least in part, on the isolated noise component.

22. An article comprising:
a non-transitory storage medium comprising machine-readable instructions which are executable by a computing platform to:
map a measurement of noise associated with a sensor signal received from a blood glucose sensor to one of three or more discrete levels or values;
select an output signal for use in estimating a blood glucose concentration from among a plurality of distinct signal-filter paths arranged concurrently based, at least in part, on the one of three or more discrete levels or values; and
generate one or more commands for transmission to an insulin delivery system for regulating a rate of fluid infusion into a body based, at least in part, on the estimate of the blood glucose concentration.

23. The article of claim 22, wherein the instructions are further executable by the computing platform to select the output signal from the at least one of the plurality of distinct signal-filter paths with no filtering in response to the measurement of noise not exceeding a threshold level.

24. The article of claim 22, wherein the instructions are further executable by the computing platform to select an output signal for use in estimating the blood glucose concentration from a different one of the plurality of distinct signal-filter paths based, at least in part, in a change in the measurement of noise.

25. The method of claim 1, wherein the plurality of distinct signal-filter paths impart differing group delays and differing noise filtering robustness.

26. A method comprising:
obtaining a sensor signal from a blood glucose sensor, the sensor signal representative of a blood glucose concentration;
selecting an output signal for use in obtaining an estimate of the blood glucose concentration from among a plurality of distinct signal-filter paths based, at least in part, on a measurement of noise associated with the signal, wherein the plurality of distinct signal-filter paths impart differing group delays and differing noise filtering robustness;
generating one or more commands for an insulin delivery system based, at least in part, on the estimate of the blood glucose concentration; and
transmitting the generated one or more commands to the insulin delivery system for regulating a rate of fluid infusion into a body.

* * * * *